US008974439B2

(12) United States Patent
Estes

(10) Patent No.: US 8,974,439 B2
(45) Date of Patent: Mar. 10, 2015

(54) INFUSION PUMP SYSTEM AND METHODS

(75) Inventor: Mark C. Estes, Calabasas, CA (US)

(73) Assignee: Asante Solutions, Inc., Sunnyvale, CA (US)

( * ) Notice: Subject to any disclaimer, the term of this patent is extended or adjusted under 35 U.S.C. 154(b) by 1835 days.

(21) Appl. No.: 12/348,162

(22) Filed: Jan. 2, 2009

(65) Prior Publication Data

US 2010/0174266 A1 Jul. 8, 2010

(51) Int. Cl.
*A61K 9/22* (2006.01)
*A61M 5/145* (2006.01)
*A61M 5/142* (2006.01)
*A61M 5/172* (2006.01)
*G06F 19/00* (2011.01)

(52) U.S. Cl.
CPC ......... *A61M 5/1456* (2013.01); *A61M 5/14244* (2013.01); *A61M 5/1723* (2013.01); *G06F 19/3468* (2013.01); *A61M 2005/14208* (2013.01); *A61M 2005/14268* (2013.01); *A61M 2005/14296* (2013.01); *A61M 2205/3592* (2013.01); *A61M 2230/201* (2013.01)
USPC ........................... 604/890.1; 604/65; 604/151

(58) Field of Classification Search
USPC ............ 604/65, 131, 66, 67, 151–155, 890.1, 604/891.1
See application file for complete search history.

(56) References Cited

U.S. PATENT DOCUMENTS

| 5,984,894 | A | 11/1999 | Poulsen et al. |
| 6,551,276 | B1 | 4/2003 | Mann et al. |
| 6,554,798 | B1 | 4/2003 | Mann et al. |
| 6,659,978 | B1 | 12/2003 | Kasuga |
| 6,691,043 | B2 | 2/2004 | Ribeiro, Jr. |
| 6,744,350 | B2 | 6/2004 | Blomquist |
| 6,852,104 | B2 | 2/2005 | Blomquist |
| 6,925,393 | B1 | 8/2005 | Kalatz et al. |
| 6,936,029 | B2 | 8/2005 | Mann et al. |

(Continued)

FOREIGN PATENT DOCUMENTS

| EP | 0-062-974 A1 | 10/1982 |
| EP | 0-275-213 A2 | 7/1988 |

(Continued)

OTHER PUBLICATIONS

European Patent Office, International search Report & Written Opinion for Application No. PCT/US2009/069937, dated May 27, 2010, 16 pages.

(Continued)

*Primary Examiner* — Aarti B Berdichevsky
*Assistant Examiner* — Laura Schell
(74) *Attorney, Agent, or Firm* — Fish & Richardson P.C.

(57) ABSTRACT

Some embodiments an infusion pump system can provide a suggested bolus dosage based on particular parameters (e.g., the user's recent blood glucose characteristics, food intake data, an amount of insulin already delivered to the user which has not yet acted on the user, or other factors). In some circumstances, the infusion pump system can receive information indicative of the user's blood glucose level and suggest an insulin bolus dosage that is at least partially dependent upon the recent rate of change in the user's blood glucose level. Such a feature can be helpful to a user when the infusion pump is operated in conjunction with a glucose monitoring device because the suggested bolus dosage can be at least partially based on recent data indicative of the user's blood glucose level.

4 Claims, 14 Drawing Sheets

(56) References Cited

U.S. PATENT DOCUMENTS

| | | |
|---|---|---|
| 6,979,326 B2 | 12/2005 | Mann et al. |
| 6,997,920 B2 | 2/2006 | Mann et al. |
| 7,025,743 B2 | 4/2006 | Mann et al. |
| 7,109,878 B2 | 9/2006 | Mann et al. |
| 7,278,983 B2 | 10/2007 | Ireland et al. |
| 7,291,107 B2* | 11/2007 | Hellwig et al. ............... 600/365 |
| 2004/0167464 A1 | 8/2004 | Ireland et al. |
| 2004/0176720 A1 | 9/2004 | Kipfer |
| 2006/0173406 A1* | 8/2006 | Hayes et al. .................... 604/67 |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0118405 A1 | 5/2007 | Campbell et al. |
| 2007/0167912 A1 | 7/2007 | Causey et al. |
| 2007/0173761 A1* | 7/2007 | Kanderian et al. ............ 604/131 |
| 2007/0179444 A1 | 8/2007 | Causey et al. |
| 2008/0125700 A1 | 5/2008 | Moberg et al. |
| 2008/0177165 A1* | 7/2008 | Blomquist et al. ............ 600/365 |
| 2008/0294094 A1 | 11/2008 | Mhatre et al. |
| 2008/0294142 A1* | 11/2008 | Patel et al. .................... 604/506 |
| 2008/0924094 | 11/2008 | Mhatre et al. |
| 2008/0306434 A1* | 12/2008 | Dobbles et al. ................. 604/66 |

FOREIGN PATENT DOCUMENTS

| | | |
|---|---|---|
| EP | 1-045-146 A2 | 12/2000 |
| EP | 1 818 664 A | 8/2007 |
| WO | WO 2004/056412 A2 | 7/2004 |
| WO | WO 2004/110526 A | 12/2004 |

OTHER PUBLICATIONS

"Which Insulin Pump is Right for Me?", Albany Medical Center, Goodman Diabetes Service, Jan. 2006, 4 pages.

"Using the Deltec Cozmo Insulin Pump Correction Bolus Feature" believed to be publicly available before May 5, 2008, pp. 36-41.

* cited by examiner

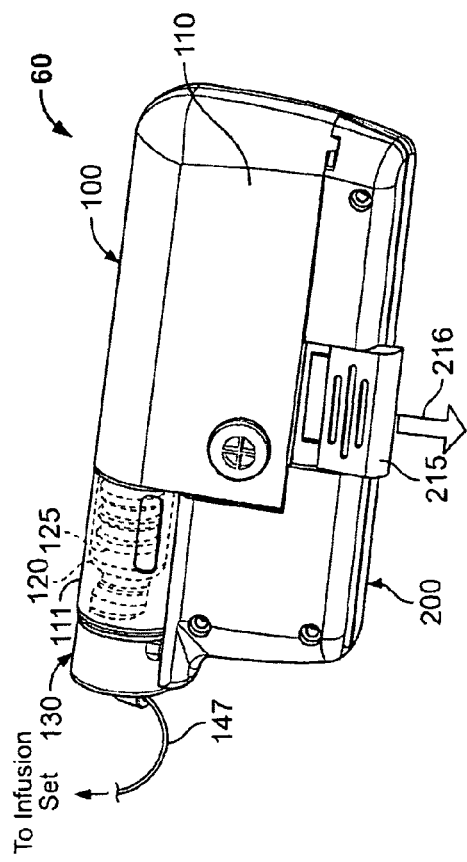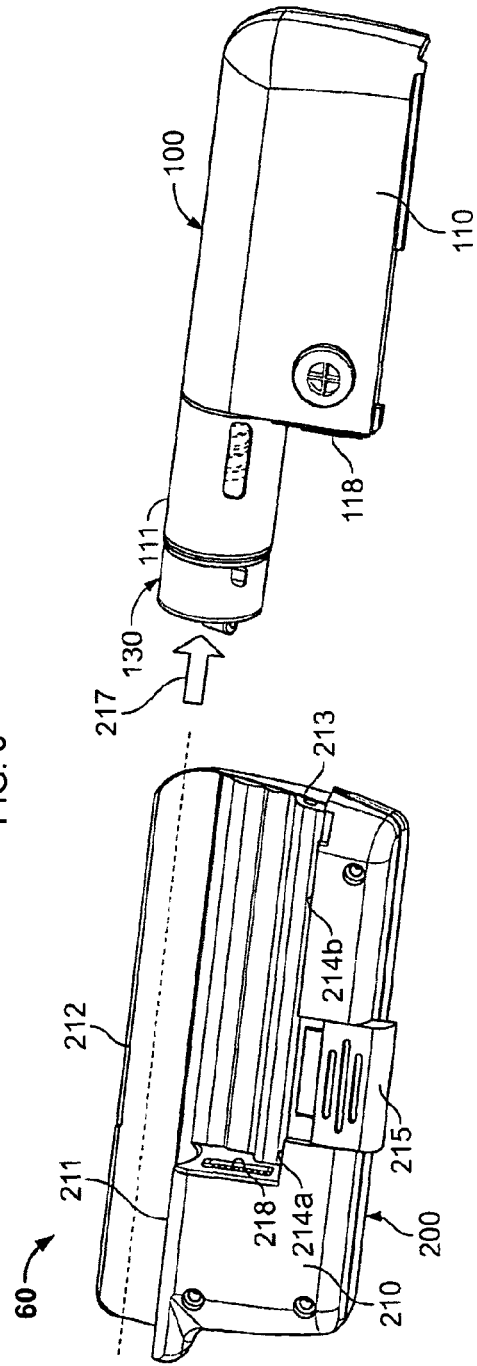

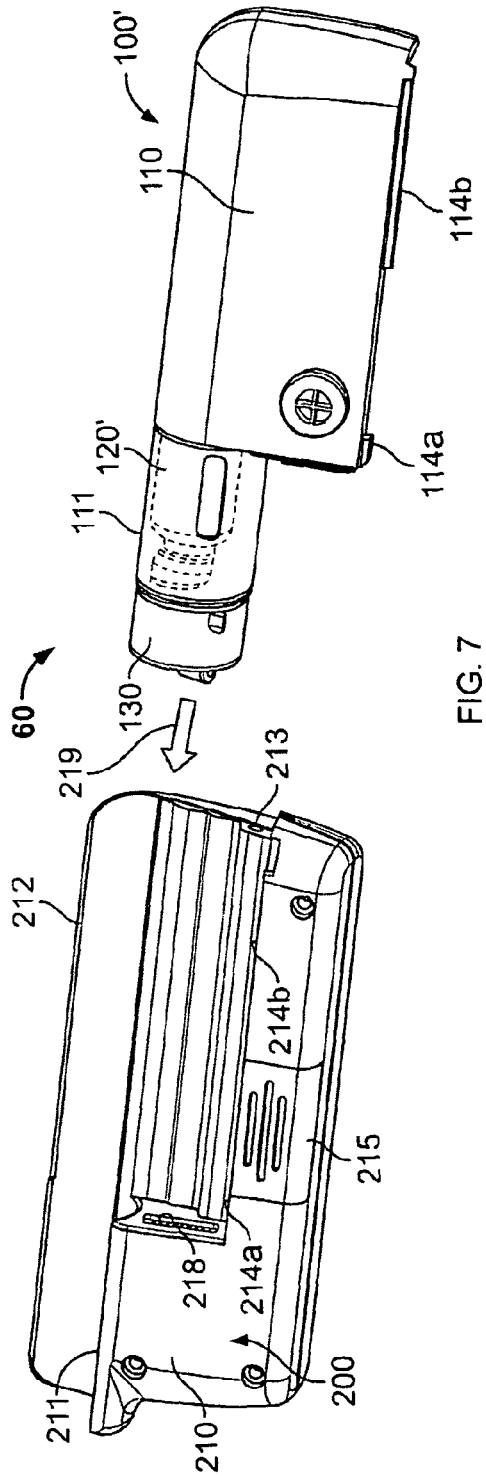
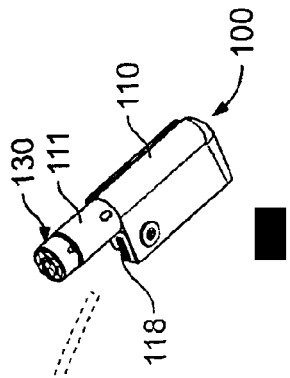
FIG. 7
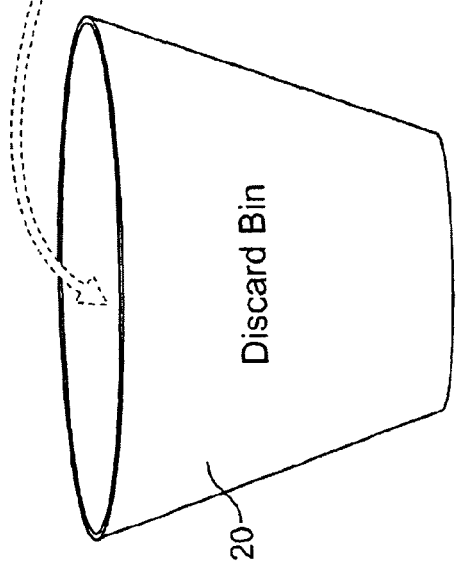
FIG. 8

INFUSION PUMP SYSTEM AND METHODS

TECHNICAL FIELD

This disclosure relates to portable infusion pump systems to deliver fluids, such as insulin infusion pump systems or the like.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels. In some circumstances, the dosage of medicine delivered by the infusion pump can be calculated by the infusion pump system. In these circumstances, the infusion pump system can take into account many variables, including user input, when making such calculations.

SUMMARY

Some embodiments an infusion pump system can provide a suggested bolus dosage based on particular parameters (e.g., the user's recent blood glucose characteristics, food intake data, an amount of insulin already delivered to the user which has not yet acted on the user, and the like). In some circumstances, the infusion pump system can receive information indicative of the user's blood glucose level and suggest an insulin bolus dosage that is at least partially dependent upon the recent rate of change in the user's blood glucose level. Such a bolus suggestion feature can be initiated, for example, by the infusion pump system in response to input of food intake information that is indicative of a recently or soon-to-be consumed meal. Accordingly, the suggested bolus dosage can vary depending on one or more of these parameters. Such a feature can be helpful to a user when the infusion pump is operated in conjunction with a glucose monitoring device because the suggested bolus dosage can be at least partially based on recent data indicative of the user's blood glucose level.

Particular embodiments of a medical infusion pump system may include a portable pump housing that receives insulin for dispensation to a user. The pump housing may at least partially contain a pump drive system to dispense the insulin through a flow path to the user. The system may also include a controller that communicates with the pump drive system to dispense the insulin from the portable pump housing. Also, the system may include a monitoring device that communicates glucose information to the controller, and the glucose information may be indicative of a blood glucose level of the user. The controller may display a suggested bolus dosage in response to user input. In such systems, the suggested bolus dosage may be at least partially dependent upon both the blood glucose level of the user and a rate of change to the blood glucose level of the user.

In some embodiments, a method of operating an insulin infusion pump system may include receiving glucose information indicative of a blood glucose level of a user. Also, the method may include, in response to receiving user input indicative of a quantity of food intake, determining a suggested bolus dosage according to a calculation that is at least partially dependent upon (i) the user input indicative of a quantity of food intake, (ii) the blood glucose level of the user, and (iii) a rate of change in the blood glucose level of the user. The method may further include displaying on a display screen a combination of the suggested bolus dosage, the blood glucose level of the user, and an indication that the rate of change in the blood glucose level in increasing or decreasing. The method may also include dispensing the suggested bolus dosage in accordance with a predetermined protocol in response to a user command.

These and other embodiments described herein may provide one or more of the following advantages. First, some embodiments of an infusion pump system that accurately calculates a suggested bolus dosage that accounts for not only the user's blood glucose level, but also the recent rate of change in the user's blood glucose level. For example, the infusion pump system can display a suggested bolus dosage to the user that is based on the user's recent blood glucose characteristics (including the rate of change in the blood glucose levels), the user's input of food intake data, an amount of insulin already delivered to the user which has not yet acted on the user, and the like.

Second, the infusion pump system can include a controller device that initiates the bolus suggestion module in response to input of food intake information that is indicative of a recently or soon-to-be consumed meal. For example, when the user inputs information indicative of a lunch meal that will be imminently consumed (e.g., carbohydrate data or the like), the controller device can prompt the user to schedule a bolus dosage of insulin to account for the effects of the lunch meal. In doing so, the controller device can display the suggested bolus dosage to the user such that the user can make an informed decision regarding the user's insulin intake. In some embodiments, the user can readily accept the suggested bolus dosage by pressing a single button on the user interface. In alternative embodiments, the user may be prompted to a separate input screen in which the user is prompted to manually input a bolus dosage (e.g., the suggested bolus dosage calculated by the controller device or a different dosage selected by the user).

Third, the bolus suggestion feature can account for the rate of change in the user's blood glucose level in different ways. For example, the "rate-of-change" parameter can be a weighted parameter that affects the suggested bolus value in different circumstances. In some embodiments, the controller device can be configured (e.g., by the user, by a health care professional, or by the manufacturer) to implement different weights for rising and falling glucose levels. Also, the controller device can be configured to implement different weights for the rate-of-change parameter depending upon the measured rate of change in the user's blood glucose levels (e.g., 0% weight if the blood glucose rate-of-change is determined to be from 0 to 1 mg/dL/min; 10% weight if the blood glucose rate-of-change is determined to be from 1 to 2 mg/dL/min; 20% weight if the blood glucose rate-of-change is determined to be from 2 to 3 mg/dL/min; and the like). Thus, when the user's blood glucose level is rising or falling at a relatively large rate, the bolus calculation module may provide a suggested bolus dosage that accounts for this trend in the user's blood characteristics.

Fourth, the infusion pump system may utilize this bolus calculation feature in combination with a glucose monitoring device that continuously transmits blood glucose information (e.g., every minute, every two minutes, every five minutes, every ten minutes, or the like) to the controller. The blood glucose information from the glucose monitoring device can be used to determine the recent rate of change in the user's blood glucose level, and the controller device can use the rate-of-change parameter to accurately calculate a suggested bolus dosage.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 5-6 are perspective views of a pump device being detached from a controller device of the system of FIG. 1, in accordance with some embodiments.

FIGS. 7-8 are perspective views of the pump device of FIGS. 5-6 being discarded and the controller device of FIGS. 5-6 being reused with a new pump device.

Like reference symbols in the various drawings indicate like elements.

DETAILED DESCRIPTION OF ILLUSTRATIVE EMBODIMENTS

Figure 1:
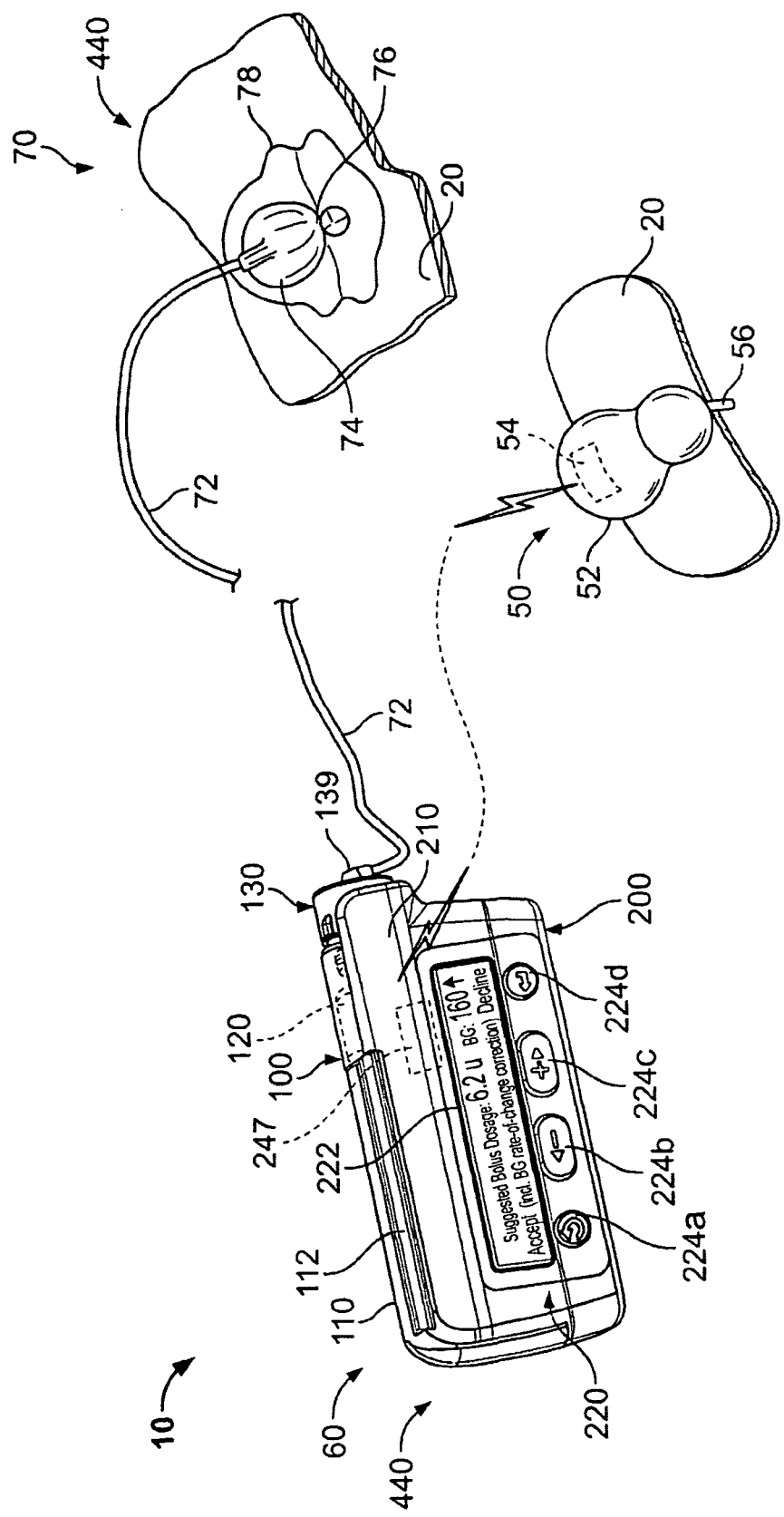
FIG. 1 is a perspective view of an infusion pump system in accordance with some embodiments.

Referring to FIG. 1, an infusion pump system 10 can include a pump assembly 60 used to supply insulin or another medication to a user via, for example, an infusion set 70. In some embodiments, the infusion pump system 10 may include a glucose monitoring device 50 that communicates with the infusion pump assembly 60 for the purpose of supplying data indicative of a user's blood glucose level to a controller device 200 included in the pump assembly 60. The infusion pump system 10 can utilize the data indicative of a user's blood glucose level in the calculation of a bolus dosage. For example, the infusion pump system 10 can calculate the recent rate of change in the user's blood glucose level and can use this rate-of-change information as a parameter in the calculation of a suggested bolus dosage for the user.

In some embodiments, the infusion pump system 10 can be configured to supply scheduled basal dosages of insulin (or another medication) along with user-selected bolus dosages. The basal delivery rate can be selected to maintain a user's blood glucose level in a targeted range during normal activity when the user is not consuming food items. The user-selected bolus deliveries may provide substantially larger amounts of insulin in particular circumstances, such as when the user consumes food items, when the user's blood glucose level increases beyond a safe limit, when the user's blood glucose level rises faster than a threshold rate, or other scenarios in which the blood glucose level requires a significant correction. In some embodiments, the infusion pump system 10 may modify a bolus delivery (e.g., a bolus delivery after the user consumes a meal) in response to certain circumstances. For example, the infusion pump system 10 may decrease or otherwise modify a post-meal bolus delivery based on a rapidly falling blood glucose level, a current blood glucose level that is below a threshold limit, a detection of a high level of physical activity, or the like.

As described in more detail below, the infusion pump system 10 can suggest a bolus dosage to the user based, at least in part, on the user's "insulin load." As described herein, "insulin load" includes an estimated value of previously dispensed insulin that has not yet acted in the user's body, such as total insulin load (TIL) information (e.g., an insulin load calculation that includes previous basal and bolus dosages, previously consumed food, or the like), traditional insulin-on-board estimates (which typically account for only bolus dosages), or other such estimated insulin load values. Due in part to pharmacokinetic effects (e.g., the time it takes for insulin to enter the blood stream from the subcutaneous point of delivery) and pharmacodynamic effects (e.g., the time it takes for a concentration of insulin in the blood to have the physiological effect of lower blood glucose level), basal and bolus insulin dispensed into the user's system may not act instantaneously, but instead may act over a period of time to control the user's blood glucose level. As such, the user's body may include some amount of insulin that has not yet acted even while the infusion pump assembly 60 is activated to deliver additional dosages (basal, bolus, or a combination thereof). In these circumstances, the infusion pump assembly 60 can be used to determine a user's insulin load, which can provide an estimate of the insulin which was delivered but has not yet acted in the user's body. This insulin load information can be used as a parameter in the calculation of the suggested bolus dosage.

In some embodiments, the controller device 200 can a suggest bolus dosage to the user in a manner that accounts for the user's food intake, the user's blood glucose information (including the rate of change in the blood glucose level), and previously delivered insulin that has not acted on the user. As described in more detail below, this process for determining a suggested bolus dosage can accurately reflect food intake data entered into the controller device 200 by the user, the user's recent blood glucose level (e.g., input into the controller device 200 by the user, transmitted to the controller device 200 from the monitoring device 50, transmitted from an external blood glucose meter, or the like), the recent rate of change in the user's blood glucose level, and the user's insulin load. For example, a user's can enter a carbohydrate value indicative of a meal into the controller device 200, and in response thereto, the controller device 200 can output a suggested bolus dosage to the user. As described in more detail below, the controller device 200 can determine the bolus dosage based on the amount of carbohydrates consumed (or to be consumed) by the user at a meal. However, the user can benefit from an infusion pump system 10 that also takes into account other parameters so that a more accurate bolus dosage can be suggested. For example, the controller device 200 can be configured to provide a more accurate bolus dosage suggestion by accounting for the user's blood glucose level and the rate of change in the user's blood glucose level Referring now to FIGS. 1-2, the infusion pump assembly 60 can include a pump device 100 and the controller device 200 that communicates with the pump device 100. The pump device 100 includes a housing structure 110 that defines a cavity 116 in which a fluid cartridge 120 can be received. The pump device 100 also includes a cap device 130 to retain the fluid cartridge 120 in the cavity 116 of the housing structure 110. The pump device 100 includes a drive system (described in more detail below in connection with FIG. 10) that advances a plunger 125 in the fluid cartridge 120 so as to dispense fluid therefrom. In some embodiments, the dispensed fluid exits the fluid cartridge 120, passes through a flexible tube 72 of the infusion set 70 to a cannula housing 74. The dispensed fluid can enter through the skin via a cannula 76 attached to the underside of the cannula housing 74.

In some embodiments, the controller device 200 communicates with the pump device 100 to control the operation of the pump drive system. When the controller device 200, the pump device 100 (including the cap device 130 in this embodiment), and the fluid cartridge 120 are assembled together, the user may conveniently wear the infusion pump assembly 60 on the user's skin under clothing or in the user's pocket while receiving the fluid dispensed from the pump device 100 (refer, for example, to FIGS. 3-4). Thus, in some embodiments, the pump assembly can operate as a portable unit that provides reliable delivery of insulin or another medication in a discrete manner.

As described in more detail below, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 to the reusable controller device 200 for the dispensation of fluid from a new fluid cartridge 120. Accordingly, the user is permitted to reuse the controller device 200 (which may include complex or valuable electronics) while disposing of the relatively low-cost pump device 100 after each use. Such a pump assembly 60 can provide enhanced user safety as a new pump device 100 (and drive system therein) is employed with each new fluid cartridge 120.

Referring again to FIG. 1, the glucose monitoring device 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In response to the measurements made by the sensor shaft 56, the glucose monitoring device 50 can employ the wireless communication device 54 to transmit data to the controller device 200 of the pump assembly 60.

In some embodiments, the monitoring device 50 may include a circuit that permits sensor signals (e.g., data from the sensor shaft 56) to be communicated to the communication device 54. The communication device 54 can transfer the collected data to the infusion pump assembly 60 (e.g., by wireless communication to a communication device 247 arranged in the pump assembly 60). In some embodiments, the monitoring device 50 can employ other methods of obtaining information indicative of a user's blood characteristics and transferring that information to the infusion pump assembly 60. For example, an alternative monitoring device may employ a micropore system in which a laser porator creates tiny holes in the uppermost layer of a user's skin, through which interstitial glucose is measured using a patch. Alternatively, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level.

Furthermore, it should be understood that in some embodiments, the monitoring device 50 can be in communication with the pump assembly 60 via a wired connection. In other embodiments of the pump system 10, test strips (e.g., blood test strips) containing a sample of the user's blood can be inserted into a strip reader portion of the pump assembly 60 to be tested for characteristics of the user's blood. Alternatively, the test strips (e.g., glucose test strips) containing a sample of the user's blood can be inserted into a glucose meter device (not shown in FIG. 1), which then analyzes the characteristics of the user's blood and communicates the information (via a wired or wireless connection) to the pump assembly 60. In still other embodiments, characteristics of the user's blood glucose information can be entered directly into the pump system 10 via a user interface on the controller device 200.

Briefly, in use, the pump device 100 can be configured to removably attach to the controller device 200 in a manner that provides a secure fitting, an overall compact size, and a reliable electrical connection. The compact size permits the infusion pump assembly 60 to be discrete and portable. The controller device 200 of the infusion pump system can be used to provide glucose alarms indicative of high and low blood glucose levels (when compared to predetermined high and low blood glucose alarm levels, respectively), to provide glucose alarms indicative of rapidly increasing or decreasing blood glucose levels, and to modify predetermined high and low blood glucose alarm levels based on the rate at which a user's blood glucose level is changing.

It should be understood that, in alternative embodiments, the pump device 100 and the controller device 200 can be configured as a single unit in which the control components and the pump drive system are arranged in a single housing. In these alternative embodiments, the pump assembly (including the controller device and the pump device) may have a different size and shape and may operate as a reusable unit that can communicate with a number of monitoring devices 50 over a period of time.

Referring again to FIGS. 1-2, in some embodiments, the pump system 10 is a medical infusion pump system that is configured to controllably dispense a medicine from the cartridge 120. As such, the fluid cartridge 120 may contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: medicines to treat primary immune deficiency (e.g., Vivaglobin® by CSL Behring of King of Prussia, Pa.), pain relief drugs, hormone therapy, blood pressure treatments, anti-emetics, osteoporosis treatments, or other injectable medicines. In some circumstances, the user may receive a scheduled, substantially continuous, basal rate of medicine from the fluid cartridge 120. In addition, or in the alternative, the user may receive intermittent, relatively larger, bolus dosages of medicine based on certain information. For example, the infusion pump assembly 60 can be used to supply a bolus dosage of insulin based on one or more meals recently entered into the controller device 200, previously received insulin, information specific to the user (e.g., insulin sensitivity), activity level, and information derived from data indicative of the user's blood glucose level. It should be understood from the description herein that the fluid cartridge 120 may have a configuration other than that depicted in FIG. 2. For example, the fluid cartridge may have a different outer shape or a different reservoir volume. In another example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

Figure 2:
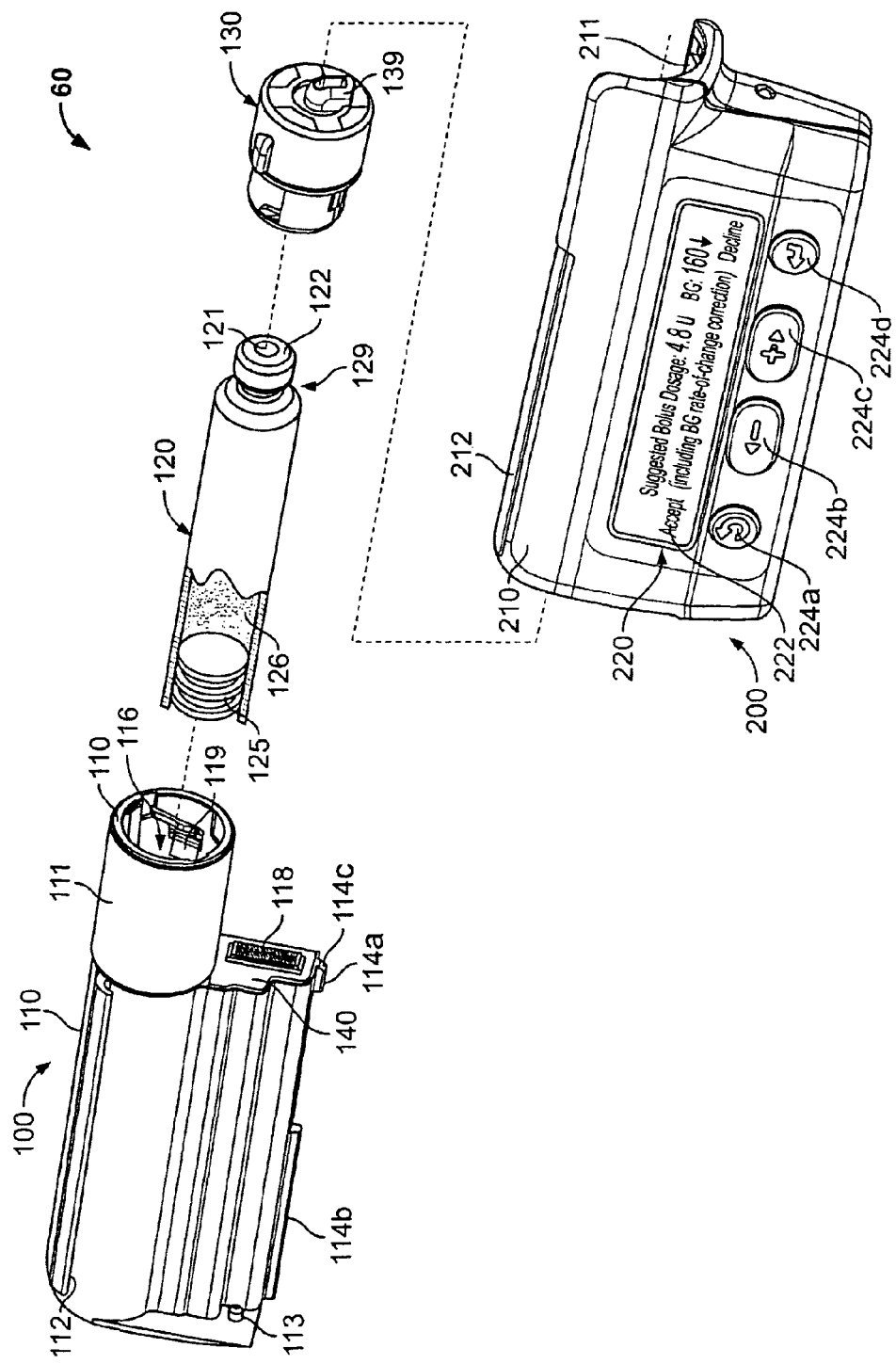
FIG. 2 is a perspective exploded view of an infusion pump assembly of the system of FIG. 1.

In some embodiments, the pump device 100 may include one or more structures that interfere with the removal of the medicine cartridge 120 after the medicine cartridge 120 is inserted into the cavity 116. For example, as shown in FIG. 2, the pump housing structure 110 may include one or more retainer wings 119 that at least partially extend into the cavity 116 to engage a portion of the medicine cartridge 120 when the medicine cartridge 120 is installed therein. In this embodiment, the pump housing structure 110 includes a pair of opposing retainer wings 119 (only one is shown in the view in FIG. 2) that flex toward the inner surface of the cavity 116 during insertion of the medicine cartridge 120. After the medicine cartridge is inserted to a particular depth, the retainer wings 119 are biased to flex outward (toward the center of the cavity 116) so that the retainer wings 119 engage a neck portion 129 of the medicine cartridge 120. This engagement with the retainer wings 119 and the neck portion 129 hinder any attempts to remove the medicine cartridge 120 away from the pump device 100. Alternative embodiments can include other features and/or configurations to hinder the removal of the medicine cartridge 120.

Embodiments of the pump device 100 that hinder the removal of the medicine cartridge 120 may facilitate the "one-time-use" feature of the pump device 100. Because the retainer wings 119 can interfere with attempts to remove the medicine cartridge 120 from the pump device 100, the pump device 100 will be discarded along with the medicine cartridge 120 after the medicine cartridge 120 is emptied, expired, or otherwise exhausted. The retainer wings 119 may serve to hinder attempts to remove the exhausted medicine cartridge 120 and to insert a new medicine cartridge 120 into the previously used pump device 100. Accordingly, the pump device 100 may operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-2, the cap device 130 can be joined with the pump device 100 after the medicine cartridge is inserted in the cavity 116. It should be understood that the cap device 130 may supplement or replace the previously described retainer wings 119 by locking into position after joining with the pump housing 110, thereby hindering removal of the fluid cartridge 120 in the pump housing 110. As shown in FIGS. 1-2, the cap device 130 may include an output port 139 that connects with the tubing 72 for dispensation of the medicine to the user. In some embodiments, the output port 139 may have an angled orientation such that a portion of the tubing extends transversely to the central axis of the cartridge 120 and cap device 130. The output port 139 can be configured to mate with tubing 72 of the infusion set 70 (FIG. 1).

In some embodiments, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (described in connection with FIG. 10) of the pump device 100. As described in more detail below, the pump device 100 includes a drive system that causes controlled dispensation of the medicine or other fluid from the cartridge 120. In some embodiments, the drive system incrementally advances a piston rod longitudinally into the cartridge 120 so that the fluid is forced out of an output end 122. The septum 121 at the output end 122 of the fluid cartridge 120 can be pierced to permit fluid outflow when the cap device 130 is connected to the pump housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

The controller device 200 may be configured to removably attach to the pump device 100, for example, in a side-by-side arrangement. The compact size permits the infusion pump assembly 60 to be discrete and portable when the pump device 100 is attached with the controller device 200 (as shown in FIG. 1). In this embodiment, the controller device 200 includes a controller housing structure 210 having a number of features that are configured to mate with complementary features of the pump housing structure 110 so as to form a releasable mechanical connection (described below in more detail in connection with FIGS. 5-7). Such mating features of the pump housing structure 110 and the controller housing structure 210 can provide a secure connection when the controller device 200 is attached to the pump device 100

As shown in FIG. 2, the pump device 100 may include an electrical connector 118 (e.g., having conductive pads, pins, or the like) that are exposed to the controller device 200 and that mate with a complementary electrical connector (refer to connector 218 in FIG. 6) on the adjacent face of the controller device 200. The electrical connectors 118 and 218 provide the electrical communication between the control circuitry (refer, for example, to FIG. 9) housed in the controller device 200 and at least a portion of the drive system or other components of the pump device 100. In some exemplary embodiments, the electrical connectors 118 and 218 permit the transmission of electrical control signals to the pump device 100 and the reception of feedback signals (e.g., sensor signals) from particular components within the pump device 100. Furthermore, as described in more detail below, the infusion pump assembly 60 may include a gasket 140 that provides a seal which is resistant to migration of external contaminants when the pump device 100 is attached to the controller device 200. Thus, in some embodiments, the pump device 100 and the controller device 200 can be assembled into a water resistant configuration that protects the electrical interconnection from water migration (e.g., if the user encounters water while carrying the pump assembly 60).

Referring again to FIGS. 1-2, the controller device 200 includes the user interface 220 that permits a user to monitor the operation of the pump device 100. In some embodiments, the user interface 220 includes a display 222 and one or more user-selectable buttons (e.g., four buttons 224a, 224b, 224c, and 224d in this embodiment). The display 222 may include an active area in which numerals, text, symbols, images, or a combination thereof can be displayed (refer, for example, to FIG. 2). For example, the display 222 may be used to communicate a number of status indicators, alarms, settings, and/or menu options for the infusion pump system 10. In some embodiments, the display 222 can indicate inform the user of the amount of a suggested bolus dosage, the user's blood glucose level, an indication that the user's blood glucose level is rising or falling, an indication that the bolus dosage suggestion includes a correction for the rate of change in the user's blood glucose level, and the like. In the example depicted in FIG. 1, the display 222 indicates a suggested bolus amount of 6.2 units, a blood glucose level of 160 mg/dL that is rising, and that the suggested bolus amount (6.2 units) includes a correction factor based on the rate of change in the user's blood glucose level. The display 222 also indicates that the user can accept the suggested bolus amount by activating the button 224a or decline it by activating the button 224d.

In some embodiments, the user may press one or more of the buttons 224a, 224b, 224c, and 224d to shuffle through a number of menus or program screens that show particular status indicators, settings, and/or data (e.g., review data that shows the medicine dispensing rate, the amount of medicine delivered during the last bolus, the delivery time of the last bolus, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time. In another example, the user may use the buttons 224a-d to manually input information such as the user's current blood glucose level (e.g., as measured by an external blood glucose meter), the current rate of change in the user's blood glucose level, or the like into the pump system 10.

The display 222 of the user interface 220 may be configured to display information when no buttons 224a, 224b, 224c, and 224d have been pressed. For example, as shown in FIG. 2, the active area of the display 222 can display a suggested bolus dosage calculated by the controller device 200 and an indication that the bolus dosage suggested includes a blood glucose rate of change correction. The display 222 can also display the user's blood glucose level (160 mg/dl in this example) and an indication of whether the user's blood glucose level is rising or falling (the downward facing arrow indicates a falling glucose level in this example). In addition to this information, the user interface may prompt the user to accept or decline the bolus suggestion (e.g., by pressing button 224a or 224d, respectively) or to enter a modified bolus amount. This information can be displayed until one of the buttons 224a or 224d has been actuated. This, or other, information can also be displayed for a period of time after no button 224a, 224b, 224c, and 224d has been actuated (e.g., five seconds, 10 seconds, 30 seconds, 1 minute, 5 minutes, or the like). Thereafter, the display 222 may enter sleep mode in which the active area is blank, thereby conserving battery power. In addition or in the alternative, the active area can display particular device settings, such as the current dispensation rate or the total medicine dispensed, for a period of time after no button 224a, 224b, 224c, or 224d has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224a, 224b, 224c, or 224d has been actuated (e.g., after 15 seconds or the like), and then the display 22 can enter sleep mode and become blank after a second period of time in which no button 224a, 224b, 224c, or 224d has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the display 222 of the controller device 200. Such monitoring capabilities may provide comfort to a user who may have urgent questions about the current operation of the pump device 100 (e.g., the user may be unable to receive immediate answers if wearing an infusion pump device having no user interface attached thereto). Moreover, information related to the last delivered bolus can be displayed contemporaneously with the detected blood glucose value and an indication of whether the user's blood glucose level is rising or falling, so the user is provided with the opportunity to make informed decisions regarding the current and future status of his or her blood glucose level.

Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200 without the requirement of locating and operating a separate monitoring module.

In other embodiments, the user interface 200 is not limited to the display and buttons depicted in FIGS. 1-2. For example, in some embodiments, the user interface 220 may include only one button or may include a greater numbers of buttons, such as two buttons, three buttons, four buttons, more than four buttons, a full QWERTY keyboard, or the like. In another example, the user interface 220 of the controller device 200 may include a touch-sensitive screen so that a user may select buttons defined by the active area of the touch screen display. Alternatively, the user interface 220 may comprise audio inputs or outputs so that a user can monitor (e.g., through audio coming from the user interface 220) and/or modify (e.g., through voice commands) the operation of the pump device 100.

Figure 3:
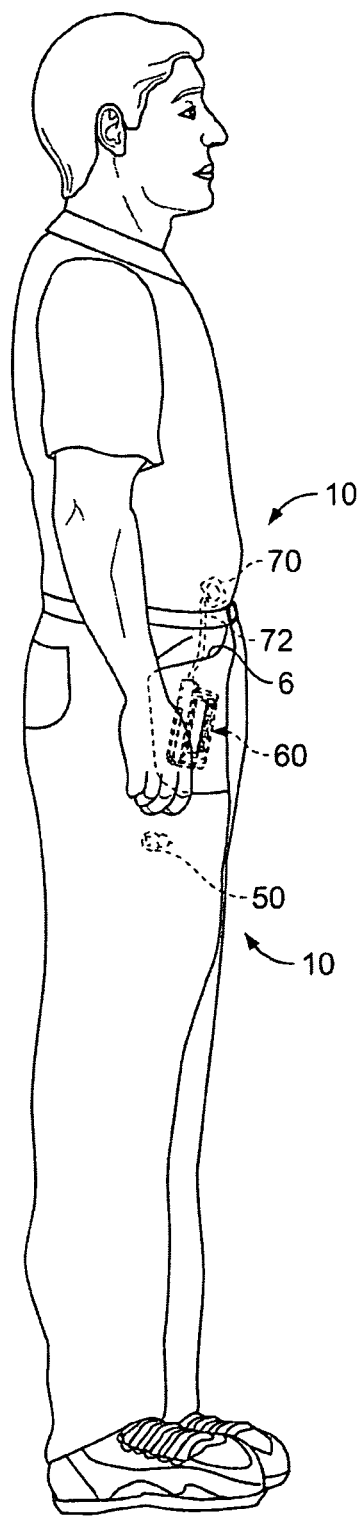
FIG. 3 is a perspective view of the infusion pump system of FIG. 1 in which the pump assembly is worn on clothing of a user, in accordance with particular embodiments.
Figure 4:
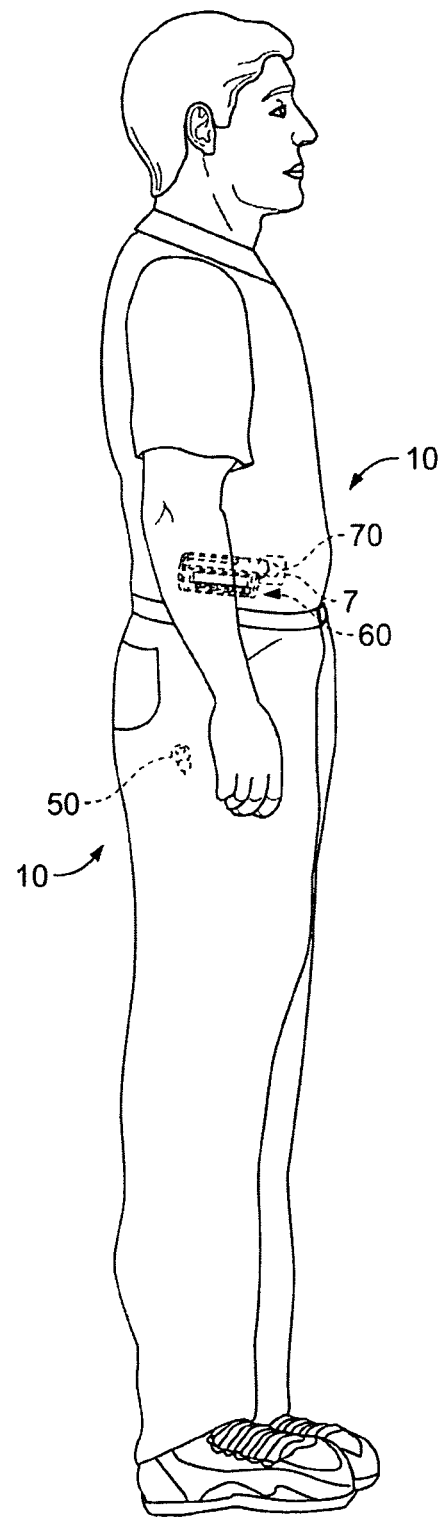
FIG. 4 is a perspective view of an infusion pump system of FIG. 1 in which the pump assembly is worn on skin of a user, in accordance with other embodiments.

Referring to FIGS. 3-4, the infusion pump system 10 may be configured to be portable and can be wearable and concealable. For example, a user can conveniently wear the infusion pump assembly 60 on the user's skin (e.g., skin adhesive) underneath the user's clothing or carry the pump assembly 60 in the user's pocket (or other portable location) while receiving the medicine dispensed from the pump device 100. The pump device 100 may be arranged in a compact manner so that the pump device 100 has a reduced length. For example, in the circumstances in which the medicine cartridge 120 has a length of about 7 cm or less, about 6 cm to about 7 cm, and about 6.4 cm in one embodiment, the overall length of the pump housing structure 110 (which contains medicine cartridge and the drive system) can be about 10 cm or less, about 7 cm to about 9 cm, and about 8.3 cm in one embodiment. In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump assembly 60 (including the removable controller device 200 attached to the pump device 100 having the cap 130) may have an overall length of about 11 cm or less, about 7 cm to about 10 cm, and about 9.6 cm in one embodiment; an overall height of about 6 cm or less, about 2 cm to about 5 cm, and about 4.3 cm in one embodiment; and an overall thickness of about 20 mm or less, about 8 mm to about 20 mm, and about 18.3 mm in one embodiment.

The pump system 10 is shown in FIGS. 3-4 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 may be configured to mate with the infusion set 70. In general, the infusion set 70 is tubing system that connects the infusion pump system 10 to the tissue or vasculature of the user (e.g., to deliver medicine into the user's subcutaneous tissue or vasculature). The infusion set 70 may include the flexible tube 72 that extends from the pump device 100 to the subcutaneous cannula 76 retained by a skin adhesive patch 78 that secures the subcutaneous cannula 76 to the infusion site. The skin adhesive patch 78 can retain the infusion cannula 76 in fluid communication with the tissue or vasculature of the patient so that the medicine dispensed through the tube 72 passes through the cannula 76 and into the user's body. The cap device 130 may provide fluid communication between the output end 122 (FIG. 2) of the medicine cartridge 120 and the tube 72 of the infusion set 70. For example, the tube 72 may be directly connected to the output port 139 (FIG. 2) of the cap device 130. In another example, the infusion set 70 may include a connector (e.g., a Luer connector or the like) attached to the tube 72, and the connector can then mate with the cap device 130 to provide the fluid communication to the tube 72. In these examples, the user can carry the portable infusion pump assembly 60 (e.g., in the user's pocket, connected to a belt clip, adhered to the user's skin, or the like) while the tube 72 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module.

Referring to FIG. 3, in some embodiments, the infusion pump assembly 60 is pocket-sized so that the pump device 100 and controller device 200 can be worn in the user's pocket 6 or in another portion of the user's clothing. For example, the pump device 100 and the controller device 200 can be attached together and form the assembly 60 that comfortably fits into a user's pocket 6. The user can carry the portable infusion pump assembly 60 and use the tube 72 of the infusion set 70 to direct the dispensed medicine to the desired infusion site. In some circumstances, the user may desire to wear the pump assembly 60 in a more discrete manner. Accordingly, the user may pass the tube 72 from the pocket 6, under the user's clothing, and to the infusion site where the adhesive patch 78 is positioned. As such, the pump system 10 can be used to deliver medicine to the tissues or vasculature of the user in a portable, concealable, and discrete manner. Furthermore, the monitoring device 50 can be worn on the user's skin while the pump assembly 60 is carried by the user (e.g., in a pocket). As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

Referring to FIG. 4, in other embodiments, the infusion pump assembly 60 may be configured to adhere to the user's skin 7 directly at the location in which the skin is penetrated for medicine infusion. For example, a rear surface of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 76 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220. Furthermore, the monitoring device 50 can be worn on the user's skin while the pump assembly 60 is worn on the user's skin in a different location from that where the monitoring device is worn. As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

In the embodiments depicted in FIGS. 3-4, the monitoring device 50 adheres to the user's skin 7 at the location in which the skin is penetrated by the sensor shaft 56 (to detect blood glucose levels). The sensor shaft 56 (refer to FIG. 1) penetrates the skin surface for the purpose of exposing the tip portion of the sensor shaft 56 to the tissue or the vasculature of the user. The sensor shaft 56 can detect information indicative of the user's blood glucose level and transfer this information to a circuit that is connected to the communications device 54 located within the monitoring device 50. The communication device 54 can be in wireless communication with the communication device 247 (described in connection with FIG. 9) included in the controller device 200 of the pump assembly 60.

Referring now to FIGS. 5-8, in some embodiments, the infusion pump assembly 60 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, in some embodiments, the medicine cartridge 120 containing insulin may have an expected usage life about 7 days after the cartridge is removed from a refrigerated state and the septum 121 (FIG. 2) is punctured. In some circumstances, the dispensation pattern (e.g., basal rate, bolus dosages, or the like) can cause the insulin to be emptied from the medicine cartridge 120 before the 7-day period. If the insulin is not emptied from the medicine cartridge 120 by the end of the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 may be designed to have an expected operational life of about 1 year to about 7 years, about 2 years to about 6 years, or about 3 years to about 5 years—depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new fluid cartridge 120.

Referring to FIGS. 5-6, the pump device 100 can be readily removed from the controller device 200 when the medicine cartridge 120 is exhausted. As previously described, the medicine cartridge 120 is arranged in the cavity 116 (FIG. 2) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length.

As shown in FIG. 5, the pump device 100 has been used to a point at which the medicine cartridge 120 is exhausted. The plunger 125 has been advanced, toward the left in FIG. 5, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 to determine if the medicine cartridge 120 is almost empty. When the user determines that a new medicine cartridge 120 should be employed, the pump device 100 can be readily separated from the controller device 200 by actuating a release member 215. In this embodiment, the release member 215 is a latch on the controller device 200 that is biased toward a locking position to engage the pump device 100. The latch may be arranged to engage one or more features on a lateral side of the pump housing 110. As such, the user may actuate the release member 215 by moving the release member 215 in a lateral direction 216 (FIG. 5) away from the pump device 100 (e.g., by applying a force with the user's finger).

As shown in FIG. 6, when the release member 215 is actuated and moved to a position away from the pump device 100, a segmented guide rail 114a-b is free to slide longitudinally in a guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 2) may be withdrawn from the mating depression 213 (FIG. 6), and the electrical connector 118 can be separated from the mating connector 218. In these circumstances, the pump device 100 is physically and electrically disconnected from the controller device 200 while the pump device retains the exhausted medicine cartridge 120. It should be understood that, in other embodiments, other features or connector devices can be used to facilitate the side-by-side mounting arrangement. These other features or connector devices may include, for example, magnetic attachment devices, mating tongues and grooves, or the like.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., moved in the lateral direction 216 in the embodiment shown in FIG. 5). Accordingly, in some embodiments, the pump device 100 can automatically and sharply move a small distance (e.g., about 0.5 mm to about 5 mm) away from the controller device 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Referring to FIGS. 7-8, the same controller device 200 can be reused with a new pump device 100' having a new medicine cartridge 120' retained therein, and the previously used pump device 100 can be discarded with the exhausted medicine cartridge 120. The new pump device 100' (FIG. 7) can have a similar appearance, form factor, and operation as the previously used pump device 100 (FIGS. 5-6), and thus the new pump device 100' can be readily attached to the controller device 200 for controlled dispensation of medicine from the new medicine cartridge 120'. In some embodiments, the user may prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 2). Although the tubing 72 of the infusion set 70 is not shown in FIG. 7, it should be understood that the tubing 72 may be attached to the cap device 130 prior to the cap device 130 being joined with the housing 110. For example, a new infusion set 70 can be connected to the cap device 130 so that the tubing 72 can be primed (e.g., a selected function of the pump device 100 controlled by the controller device 200) before attaching the infusion set patch to the user's skin. As shown in FIG. 7, the new medicine cartridge 120' may be filled with medicine such that the plunger 125 is not viewable through the barrel 111. In some embodiments, the user can removably attach the pump device 100 to the controller device 200 by moving the pump device 100 in a longitudinal direction 219 toward the controller device 200 such that the segmented guide rail 114a-b engages and slides within the guide channel 214a-b. When the electrical connectors 118 and 218 mate with one another, the release member 215 can engage the segmented guide rails 114a-b to retain the pump device 100 with the controller device 200.

As shown in FIG. 8, the previously used pump device 100 that was separated from the controller device 200 (as described in connection with FIGS. 5-6) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 30, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 70 (not shown in FIG. 8, refer to FIG. 1) that was used with the pump device 100 may be removed from the user and discarded into the bin 30 along with the pump device 100. Alternatively, the infusion set 70 can be disconnected from the previous pump device 100 and attached to the new pump device 100'. In these circumstances, the user may detach the infusion set cannula 76 and patch 78 from the skin so as to "re-prime" the tubing with medicine from the new pump device 100' to remove air pockets from the tubing. Thereafter, the infusion set cannula 76 and patch 78 can be again secured to the user's skin.

Figure 9:
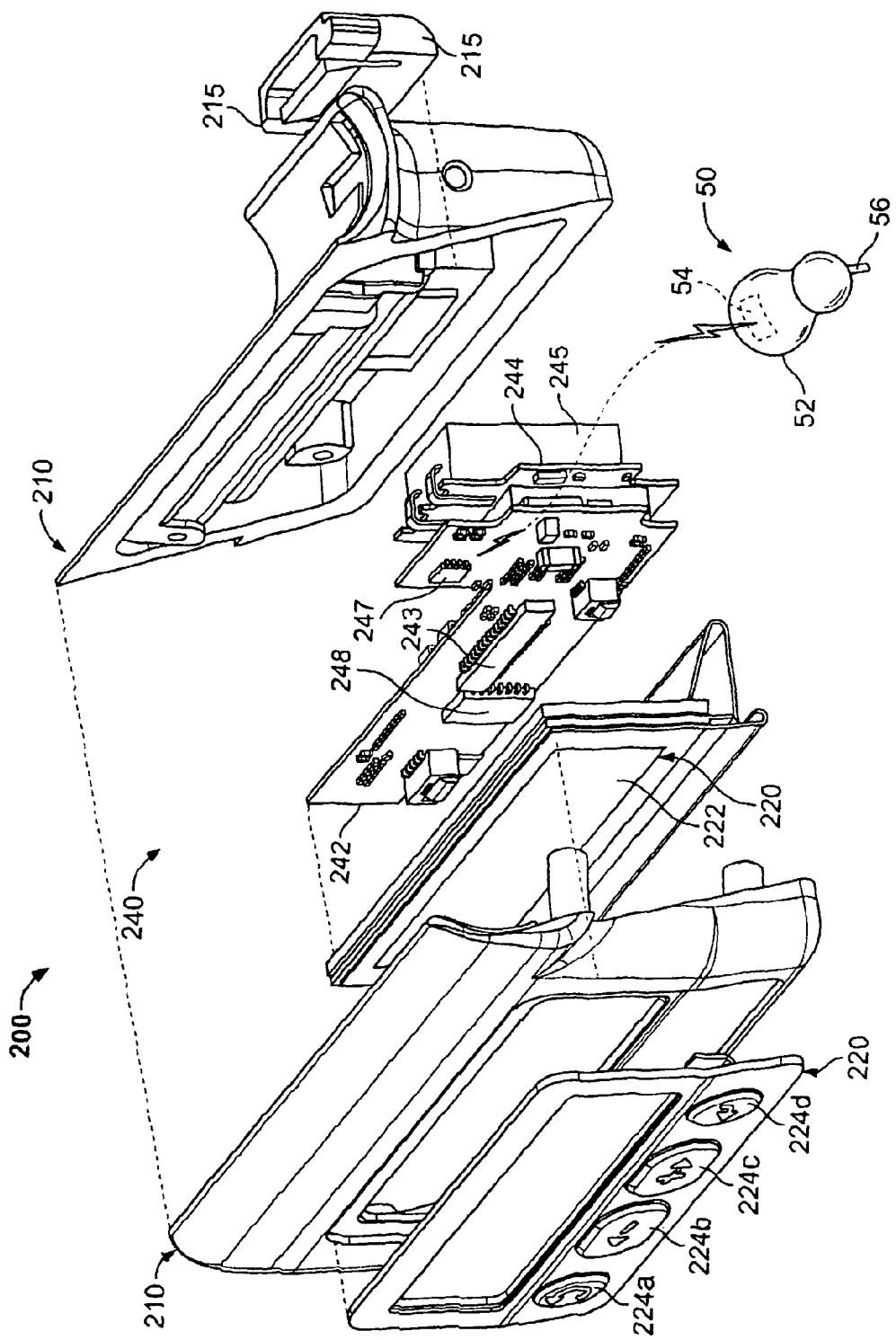
FIG. 9 is an exploded perspective view of a controller device for an infusion pump system, in accordance with some embodiments.

Referring now to FIG. 9, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as memory devices (e.g., memory chip 248). It should be understood that, although the main processor board 242 is depicted as a printed circuit board, the main processor board can have other forms, including multiple boards, a flexible circuit substrate, and other configurations that permit the processor 243 to operate.

In some embodiments, the control circuitry 240 can be programmable in that the user may provide one or more instructions to adjust a number of settings for the operation of the infusion pump system 10. Such settings may be stored in the one ore more memory devices, such as the memory chip 248 on the processor board 242. The control circuitry 240 may include other components, such as sensors (e.g., occlusion sensors), that are electrically connected to the main processor board 242. Furthermore, the control circuitry 240 may include one or more dedicated memory devices that store executable software instructions for the processor 243. The one or more memory devices (e.g., the memory chip 248) can also store information related to a user's blood glucose level and delivered bolus dosages over a period of time. The control circuitry 240 can also include the communication device 247 which can transmit information to and receive information from, for example, the glucose monitoring device 50, an external blood glucose meter, or the like.

As previously described, the controller device 200 can be electrically connected with the pump device 100 via mating connectors 118 and 218 so that the control circuitry 240 can communicate control signals to the pump device 100 and receive feedback signals from components housed in the pump device 100. In this embodiment, the electrical connector 118 (FIG. 2) on the pump device 100 is a z-axis connector, and the connector 218 (FIG. 6) on the controller device 200 is adapted to mate therewith. The electrical connector 218 on the controller device 200 is in communication with the control circuitry 240. As such, the processor 243 can operate according to software instructions stored in the memory device so as to send control signals to the pump device 100 via the connector 218.

Still referring to FIG. 9, the user interface 220 of the controller device 200 can include input components, output components, or both that are electrically connected to the control circuitry 240. For example, in this embodiment, the user interface 220 includes a display device 222 having an active area that outputs information to a user and four buttons 224a-d that receive input from the user. Here, the display 222 may be used to communicate a number of status indicators, settings, and/or menu options for the infusion pump system 10. In some embodiments, the control circuitry 240 may receive the input commands from the user's button selections and thereby cause the display device 222 to output a number of status indicators (e.g., if the pump system 10 is delivering insulin, if the user's blood glucose level is rising or falling, and the like), menus, and/or program screens that show particular settings and data (e.g., the user's blood glucose level, the time of the last bolus delivery, the amount of the last bolus delivery, or the like). As previously described, the controller circuit 240 can be programmable in that the input commands from the button selections can cause the controller circuit 240 to change any one of a number of settings for the infusion pump system 100.

Some embodiments of the control circuitry 240 may include a cable connector (e.g., a USB connection port, another data cable port, or a data cable connection via the electrical connection 218) that is accessible on an external portion of the controller housing 210. As such, a cable may be connected to the control circuitry 240 to upload data or program settings to the controller circuit or to download data from the control circuitry 240. For example, historical data of blood glucose level, blood glucose alarm limits, medicine delivery, insulin load information, or a combination thereof can be downloaded from the control circuitry 240 (via the cable connector) to a computer system of a physician or a user for purposes of analysis and program adjustments. Optionally, the data cable may also provide recharging power.

Figure 10:
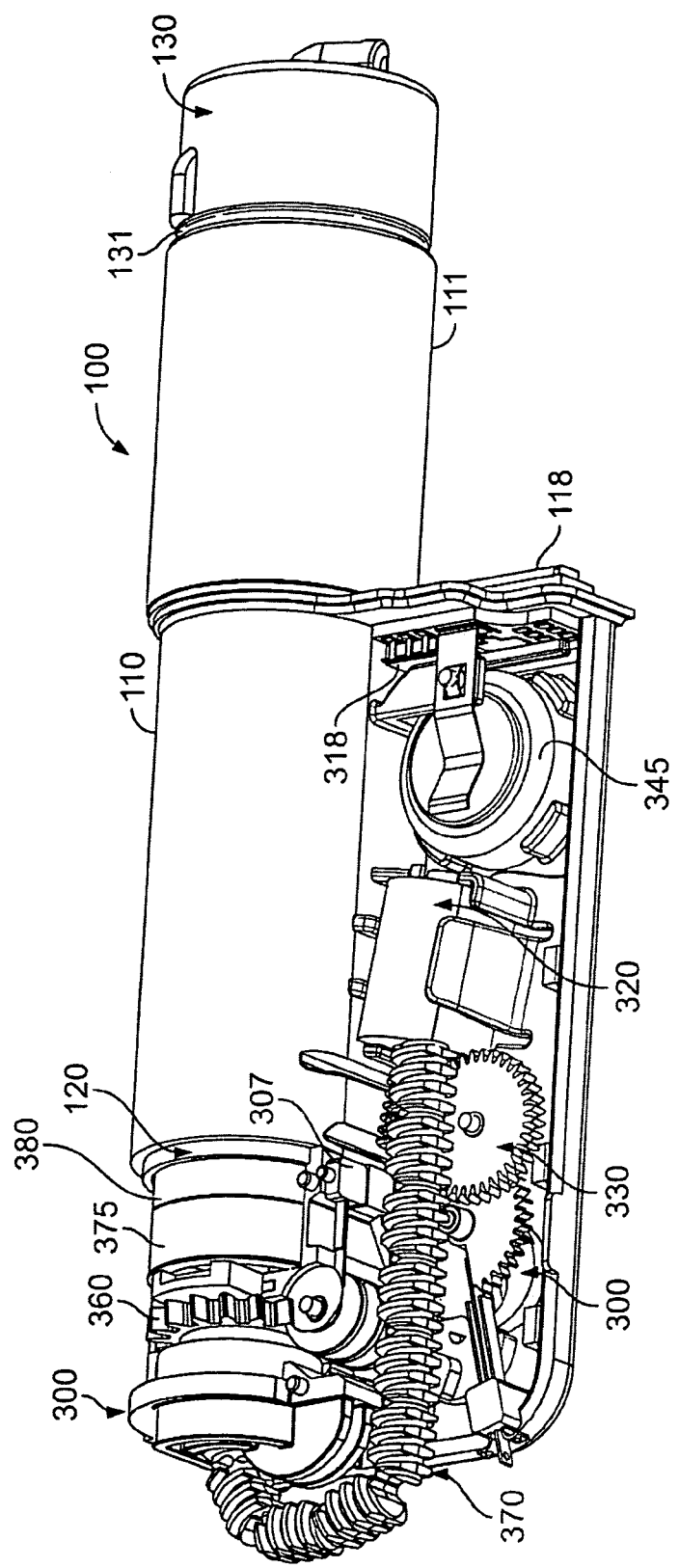
FIG. 10 is a perspective view of a portion of a pump device for an infusion pump system, in accordance with particular embodiments.

Referring to FIGS. 9-10, the control circuitry 240 of the controller device 200 may include a second power source 245 (FIG. 9) that can receive electrical energy from a first power source 345 (FIG. 10) housed in the pump device 100. In this embodiment, the second power source 245 is coupled to the power supply board 244 of the control circuitry 240. The hard-wired transmission of the electrical energy can occur through the previously described connectors 118 and 218. In such circumstances, the first power source 345 may include a high density battery that is capable of providing a relatively large amount of electrical energy for its package size, while the second power source 245 may include a high current-output battery that is capable discharging a brief current burst to power the drive system 300 of the pump device 100. Accordingly, the first battery 345 disposed in the pump device 100 can be used to deliver electrical energy over time (e.g., "trickle charge") to the second battery 245 when the controller device 200 is removably attached to the pump device 100. For example, the first battery 345 may comprise a zinc-air cell battery. The zinc-air cell battery 345 may have a large volumetric energy density compared to some other battery types. Also, the zinc-air cell battery may have a long storage life, especially in those embodiments in which the battery is sealed (e.g., by a removable seal tab or the like) during storage and before activation. In an alternative embodiment, the first battery 345 may comprise a dry-cell battery (e.g., a AAA battery or the like) that is pre-installed by a manufacturer and has a relatively large volumetric energy density as compared to the second battery 245 in the controller device 200.

The second battery 245 may include a high current-output device that is housed inside the controller housing 210. The second battery 245 can be charged over a period of time by the first battery 345 and then intermittently deliver bursts of high-current output to the drive system 300 over a brief moment of time. For example, the second battery 245 may comprise a lithium-polymer battery. The lithium-polymer battery 245 disposed in the controller device 200 may have an initial current output that is greater than the first battery 345 disposed in the pump device 100, but the first battery 345 may have an energy density that is greater than the lithium-polymer battery 245. In addition, the lithium-polymer battery 245 is readily rechargeable, which permits the first battery 345 disposed in the pump device 100 to provide electrical energy to the lithium-polymer battery 245 for purposes of recharging. In alternative embodiments, it should be understood that the second power source 245 may comprise a capacitor device capable of being recharged over time and intermittently discharging a current burst to activate the drive system 105.

Accordingly, the infusion pump system 10 having two power sources 345 and 245—one arranged in the pump device 100 and another arranged in the reusable controller device 200—permits a user to continually operate the controller device 200 without having to recharge a battery via an outlet plug-in or other power cable. Because the controller device 200 can be reusable with a number of pump devices 100 (e.g., attach the new pump device 100' after the previous pump device 100 is expended and disposed), the second power source 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Referring now to FIG. 10, the pump device 100 in this embodiment includes the drive system 300 that is controlled by the removable controller device 200 (see FIG. 2). Accordingly, the drive system 300 can accurately and incrementally dispense fluid from the pump device 100 in a controlled manner (e.g., during the substantially continuous basal delivery, the intermittent and substantially larger bolus deliveries, or the like). The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. Some embodiments of the drive system 300 may include a battery powered actuator (e.g., reversible motor 320 or the like) that actuates a gear system 330 to reset a ratchet mechanism (e.g., including a ratchet wheel and pawl), a spring device (not shown) that provides the driving force to incrementally advance the ratchet mechanism, and a drive wheel 360 that is rotated by the ratchet mechanism to advance the flexible piston rod 370 toward the medicine cartridge 120. Connected to piston rod 370 is a pusher disc 375 for moving the plunger 125 of the medicine cartridge 120.

Some embodiments of the drive system 300 can include a pressure sensor 380 disposed between the plunger engagement device 375 and the plunger 125 for determining the pressure within the fluid path (e.g., inside the medicine cartridge 120, the infusion set 70, and the like). For example, the fluid pressure in the medicine cartridge 120 can act upon the plunger 125, which in turn can act upon the pressure sensor 380 arranged on the dry side of the plunger 125. The pressure sensor 380 may comprise a pressure transducer that is electrically connected (via one or more wires) to a gateway circuit 318 so that the sensor signals can be communicated to the controller device 200 (e.g., via the electrical connectors 118 and 218). As such, data from the pressure sensor 380 can be received by the controller device 200 for use with, for example, an occlusion detection module to determine if an occlusion exists in the medicine flow path. Alternatively, the controller device 200 may include an optical sensor system (not shown in FIGS. 9-10) to detect occlusions in the fluid path. For example, a light emitter and light sensor may each be arranged on a sensor circuit in the controller device 200 (but aligned with the pump device 100) so that the light sensor can detect the amount of light emitted by the light emitter and subsequently reflected from a component adjacent the fluid path. The reflected light level detected may be used to determine the pressure within the fluid path. In this configuration, the relatively expensive light emitter and sensor are disposed in the reusable controller device 200 and, as such, can be reused with multiple pump devices 100.

Figure 11:
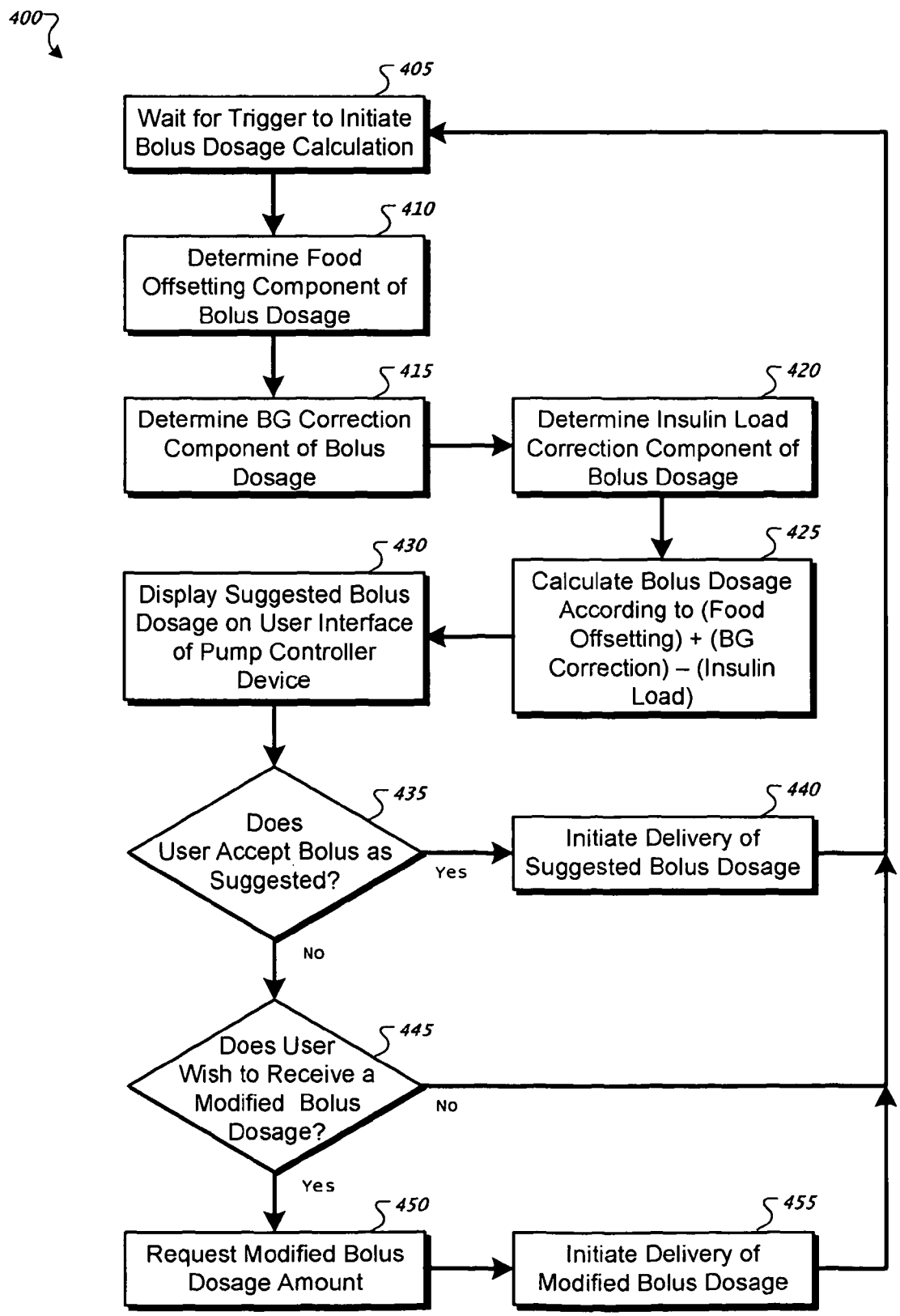
FIG. 11 is a flow diagram depicting an exemplary process used to determine a bolus dosage of insulin in response to, in part, the rate of change in a user's blood glucose level, in accordance with some embodiments.

Referring now to FIG. 11, the infusion pump system 10 can be used to calculate and suggest a bolus dosage to be delivered to the user. For example, a process 400 for calculating and displaying a suggested bolus dosage can be implemented by the controller device 200. As previously described, the pump assembly 60 can operate to deliver insulin to the user by basal dosages, selected bolus dosages, or a combination thereof A basal rate of insulin can be delivered in an incremental manner (e.g., dispense 0.25 U every fifteen minutes for a rate of 1.0 U per hour) to help maintain the user's blood glucose level within a targeted range during normal activity, when the user is not consuming food items. The user may select one or more bolus deliveries, for example, to offset the blood glucose effects caused by food intake, to correct for an undesirably high blood glucose level, to correct for a rapidly increasing blood glucose level, or the like. In some circumstances, the basal rate pattern may be programmed by a health care professional during a clinical visit (or, optionally, by the user) and may remain at a substantially constant rate for a long period of time (e.g., a first basal dispensation rate for a period of hours in the morning, and a second basal dispensation rate for a period of hours in the afternoon and evening). In contrast, the bolus dosages can be dispensed in user-selected amounts based on calculations made by the controller device 200. For example, the controller device 200 can determine that the user's blood glucose level is rapidly increasing (e.g., by interpreting data received from the glucose monitoring device 50, or the like) and can make a suggestion to the user to administer a bolus of insulin to correct for the rapid increase in blood glucose level. In another example, the user can request that the controller device 200 calculate and suggest a bolus dosage based, at least in part, on a proposed meal that the user plans to consume.

The basal and bolus insulin dispensed into the user's system may act over a period of time to control the user's blood glucose level. As such, the user can benefit from the embodiments of the infusion pump system 10 that can take into account different circumstances and information when determining the amount of a bolus dosage to suggest to the user. For example, the controller device 200 may be triggered to suggest a bolus dosage in response to the user's input of meal information. When calculating the bolus dosage, however, the user may benefit if the controller device 200 employed information, in addition to the meal information, when calculating the bolus dosage. In some embodiments, the controller device 200 can use information such as data indicative of the user's blood glucose level, food intake data recently entered into the controller device 200, the user's insulin load, and the like. Exemplary information that can be derived from the user's blood glucose information that can be used by the controller device 200 in determining a bolus dosage can include the user's current blood glucose level, the rate of change in the user's blood glucose level, the $2^{nd}$ derivative of the user's blood glucose data, the shape and/or appearance of the user's blood glucose curve, or the like. In some embodiments, the controller device 200 can use information from previously entered meals and previously delivered insulin dosages when calculating a suggested bolus dosage. In these embodiments, information regarding previously entered meals and previously delivered insulin dosages from 12 hours or more (e.g., 24 hours, 12 hours, 8 hours, 6 hours, 0.5 hours, or the like) can be used in the bolus dosage calculations.

In some embodiments, the controller device 200 may implement the process 400 (FIG. 11) to determine and suggest an insulin bolus dosage which includes a food offsetting component, a blood glucose correction component, and an insulin load correction component. The food offsetting component can represent an insulin bolus dosage to offset food intake data that have not previously been offset by an earlier bolus dosage. The blood glucose correction component can represent an insulin bolus dosage to maintain or return the user's blood glucose level to a targeted value within a predetermined range. This component can be derived from data indicative of a user's blood glucose level such as the user's current blood glucose level and the recent rate of change in the user's blood glucose level. The insulin load correction component can take into account insulin that has been previously received and food that has been previously consumed, but has not acted on the user. For example, the delay between a subcutaneous delivery of a bolus dosage of insulin and the peak plasma insulin level achieved from this bolus can be one hour or more. Additionally, the bolus dosage may not enter the subcutaneous tissue all at once. As such, the effect of the bolus can peak at about one to two hours and then decay in a predictable manner over as much as eight hours or. Due to the time decay effects of insulin activity, the user could be susceptible to request a subsequent bolus dosage while some insulin from a previously delivered bolus dosage has not yet acted upon the user (a scenario sometimes referred to as "bolus stacking"). To reduce the likelihood of undesirable bolus stacking, the insulin load information can be determined by the controller device 200 on a periodic basis so that the user can be aware of the previously dispensed insulin which has not yet acted in the user's body. In a similar manner, food that has been previously consumed does not instantaneously act on the user and have its effects quickly decay. Depending on the type of food consumed, the effects of the food can be delayed and then slowly decay over time. In particular embodiments, the insulin load correction component may correct for the delayed effects of both previously delivered insulin and previously consumed food items.

Referring in more detail to the illustrative process 400 shown in FIG. 11, the process 400 for the determining a bolus dosage to suggest to a user can include a number of operations performed by the controller device 200. In operation 405, the controller device 200 can wait for one or more triggers to initiate a bolus dosage calculation. Exemplary triggers that can cause the controller device 200 to initiate a bolus dosage calculation can include a user input of food intake data (e.g. via the user interface 220 of the controller device 200), a user input of blood glucose data (e.g., as measured by an external blood glucose meter), wireless receipt of current blood glucose information, a user request for a bolus dosage (e.g., via a menu selection on the user interface 220), the user's blood glucose level exceeding a predetermined threshold level, the user's blood glucose level increasing at a high rate greater than a predetermined threshold rate, or the like. In some embodiments, the suggested bolus dosage value can be calculated based on at least two of the three components as previously described: the food offsetting component, the blood glucose correction component, and the insulin load correction component. It should be understood from the description herein that the components can be contemporaneously calculated to provide the suggested bolus dosage value or, alternatively, calculated in discrete steps and then combined to provide the suggested bolus dosage value.

In operation 410, the controller device 200 can determine the food offsetting component of the suggested bolus dosage. In this operation, the controller device 200 can convert food intake data, such as carbohydrate information, entered into the controller device 200 and determine a quantity of insulin to offset the food intake. For example, in some embodiments, the food offsetting component can be calculated as follows:

Food Offsetting Component=(Carbohydrate Intake)*(Insulin to Carb. Ratio), where Carbohydrate Intake represents the number of grams of carbohydrates consumed and Insulin to Carb. Ratio represents a user specific ratio of the amount of insulin required to offset the consumption of a gram of carbohydrates (e.g., 15 U/g or the like).

In the embodiment described here, the user can determine the amount of carbohydrates in a meal to be consumed and then enter that carbohydrate information into the user interface 220. In some embodiments, the user can enter in the amount and types of food to be consumed and the controller device 200 can estimate the number of grams of carbohydrates from the input food information.

Still referring to FIG. 11, in operation 415, the controller device 200 can determine the blood glucose correction component of the suggested bolus dosage. In this operation, the controller device 200 can use information about the user's past and current blood glucose levels to suggest the blood glucose correction component. The blood glucose correction component can indicate an insulin amount to correct for a blood glucose level that is outside of a predetermined range (or otherwise greater than a targeted value) while also accounting for the recent rate of change of the user's blood glucose level. For example, a user with a blood glucose level of 160 mg/dL and a rapidly increasing blood glucose level may require a greater bolus insulin dosage than the same user with a blood glucose level of 160 mg/dL and a rapidly falling blood glucose level. In some embodiments, the controller device 200 can calculate the blood glucose correction component as follows:

Blood Glucose Correction Component=(Current Blood Glucose Level−Target Glucose Level)*Insulin Sensitivity*[1+(Rate of Change*Scaling Factor)], where Current Blood Glucose Level represents the most recent blood glucose level, Target Glucose Level represents the user's desired blood glucose level, Insulin Sensitivity represents a user specific value that correlates the number of units of insulin required to alter the user's blood glucose level by 1 mg/dL, and Rate of Change in represents the recent rate of change in the user's blood glucose level.

For example, a user with a current blood glucose level of 180 mg/dL, a Target blood glucose Level of 120 mg/dL, a rate of change adjustment of 0.3 (representing an increasing blood glucose level), and an Insulin Sensitivity of 0.04 (units*dL)/mg would yield a blood glucose correction component of 3.12 unit of insulin [(180−120)*(1+0.3)*0.04)], which is greater than the 2.4 units would be calculated if the rate of change adjustment was not employed in the suggested bolus calculation. As described in more detail below in connection with FIG. 14, in some circumstances, the rate of change adjustment can vary between about −0.3 and about +0.3 depending upon the recent rate of change in the user's blood glucose level.

In operation 420, the controller device 200 can determine the insulin load correction component of the suggested bolus dosage. In this operation, the controller device 200 can determine the amount of previously delivered insulin that has not yet acted on the user. The insulin that has not acted on the user can be calculated using known insulin decay curves and the food that has not acted can be calculated using, for example, a standard glycemic index. Optionally, the controller device 200 may also determine the amount of previously consumed carbohydrates that has been offset by an earlier insulin bolus but has yet not acted on the user. The previously consumed food can then be converted to a negative insulin value for the insulin load component using the user-specific insulin to carbohydrate ratio.

For example, if a user consumes a meal containing fast-acting carbohydrates (e.g., white bread, fruit juice, or the like), receives a bolus dosage of insulin, and one hour later has an elevated blood glucose level, the controller device 200 can suggest a bolus dosage to lower the user's blood glucose into a predetermined range. In this example, the controller device 200 can benefit the user by not only using the user's blood glucose information in a bolus dosage calculation, but also information regarding the prior meal and bolus delivery. In this example, a portion of the meal consumed by the user and the majority of the insulin bolus delivered to the user have not acted on the user. It is possible that the amount of insulin which has not yet acted would be enough to not only offset the food that has not acted, but also would be enough to lower the user's blood glucose level into a normal range. Thus, the controller device 200 may employ the user's insulin load when calculating a suggested bolus dosage in the future. Taking this insulin load information into account, the controller device 200 may suggest a lower dose of insulin than if the previously received bolus and previously consumed food information were not included in the calculation, potentially averting an unsafe drop in the user's blood glucose level. In some embodiments of operation 420, the controller device 200 can calculate the insulin load correction component as follows:

Insulin Load Correction Component=Insulin Load−(Carb. Load)*Insulin to Carb Ratio, where Insulin Load represents the units of previously delivered insulin that have not yet acted on the user, Carb. Load represents the grams of carbohydrates that have been consumed, but have not acted on the user's blood glucose level, and Insulin to Carb. Ratio represents a user specific ratio of the amount of insulin required to offset the consumption of a gram of carbohydrates.

As stated previously, in some embodiments of the infusion pump system 10, the controller device 200 may not include the carbohydrate load (the grams of carbohydrates that have been consumed, but have not acted on the user's blood glucose level) in the insulin load correction component calculation. As such, the insulin load correction component can be represented as an insulin-on-board estimate (which accounts only for previous bolus dosages) or a different insulin load value that accounts for both previous basal dosages and previous bolus dosages).

Still referring to FIG. 11, in operation 425, the suggested bolus dosage can be calculated by summing the food offsetting component and the blood glucose correction component and subtracting the insulin load correction bolus. For example, in some embodiments, the suggested bolus dosage may be determined as follows:

Suggested Bolus Dosage=(Food Offsetting Component)+(Blood Glucose Correction Component)−(Insulin Load Correction Component).

In these circumstances, the suggested bolus dosage may accurately reflect food intake data entered into the controller device 200, the user's blood glucose data (including the recent rate of change in the blood glucose levels), the previously dispensed insulin that has not yet acted (to reduce or otherwise effect the blood glucose level) and, optionally, the previously consumed food that has not yet been metabolized (to increase or otherwise affect the blood glucose level). It should be understood from the description herein that the components of the Suggested Bolus Dosage calculation can be contemporaneously calculated to provide the suggested bolus dosage value. In such circumstances, the operations 410, 415, and 420 can be contemporaneously executed as part of operation 425 to calculate the suggested bolus dosage. Alternatively, the components of the Suggested Bolus Dosage calculation calculated in discrete steps (e.g., separately executed operations 410, 415, and 420) and then combined in operation 425 to provide the suggested bolus dosage value.

In some alternative embodiments, the user's current rate of change in blood glucose level can be used as a parameter to modify an entire calculated bolus dosage (rather than modifying only the Blood Glucose Correction Component). For example, the Suggested Bolus Dosage in these alternative embodiments can be calculated as follows:

Suggested Bolus Dosage=[(Food Offsetting Component)+(Blood Glucose Correction Component)−(Insulin Load Correction Component)]*[1+(Rate of Change*Scaling Factor$_{roc}$)], where the (Blood Glucose Correction Component) is calculated according to (Current Blood Glucose Level−Target Glucose Level)*Insulin Sensitivity.

In this example, the user's blood glucose rate of change information can be used to modify the entire suggested bolus dosage. In another example, the rate of change information can be used to modify one or more of the individual components of the suggested bolus dosage (e.g., the food offsetting component, the blood glucose correction component, the insulin load component, or the like). In yet another example, the rate of change information can be used to modify one or more of the individual components of the suggested bolus dosage and the entire suggested bolus dosage amount.

As previously described, one component of the Suggested Bolus Dosage calculation is the Insulin Load Correction Component, which in some alternative embodiments may not account for the previous food component (as described in connection with operation 420). It should also be understood that there are, in alternative embodiments, other ways in which to calculate a suggested bolus dosage that includes information related to a recently entered meal, information related to a user's blood glucose data, information related to previously delivered insulin dosages that have not yet acted in the user's body, and (optionally) information related to previously consumed food that has not yet been metabolized.

In operation 430, the suggested bolus dosage can be displayed, for example, on the display 222 of the controller device 200. For example, the suggested bolus dosage may be communicated via the user interface 220 in response to the user's input of food intake data for a meal to be consumed. As such, the user can initiate the proper insulin bolus within a selected time frame soon before or after the meal consumption. In some embodiments, the user interface can 220 prompt the user to accept or decline the suggested bolus dosage that is displayed on the screen 222. If the user does not accept the suggested bolus dosage, the user can interact with the user interface 220 to decline or delay any bolus dosage or to select a different bolus dosage after reviewing the suggested bolus calculation.

In one example, FIG. 1 depicts shows an embodiment of the controller device 200 that is displaying a suggested bolus dosage of 6.2 units, the user's blood glucose level (160 mg/dL), an indication that the user's blood glucose is rising (up arrow), and that the bolus calculation includes a correction that accounts for the rate of change in the user's blood glucose level. The display also includes the words "Accept" and "Decline" located near buttons 224a and 224d, respectively. By pressing button 224a, the user can indicate to the controller device 200 that he or she accepts the bolus dosage as suggested. By pressing button 224d, the user can indicate to the controller device 200 that he declines the bolus dosage as suggested.

In operation 435, the controller device 200 can determine, from user input, whether the user accepted or declined the suggested bolus dosage (e.g., if the user pressed button 224a to "accept" or button 224d to "decline" as shown in the embodiment in FIG. 1). If the user accepts the suggested bolus dosage, the controller device 200 can execute operation 440, causing the pump device 100 to dispense an amount of insulin to the user that is equivalent to the suggested bolus dosage. The bolus dosage can be dispensed over a period of time according to a predetermined profile, such as a ramp profile, a square wave profile, or a curved profile. The operation of an exemplary embodiment of the pump drive system 300 to dispense the insulin dosage was described previously in connection with FIG. 10. After the suggested bolus dosage is dispensed to the user, the process 400 can then return to operation 405, where the controller device 200 can wait for a subsequent trigger to initiate another suggested bolus dosage calculations.

Revisiting operation 435 as shown in FIG. 11, if the controller device 200 receives input that indicates the user declined the suggested bolus dosage, the controller device 200 can execute operation 445 to query the user as to whether he or she intends to receive a modified bolus dosage. If the user chooses to receive a modified bolus dosage, the controller device 200 can execute operation 450, which prompts the user enter (e.g., via the user interface 220) the modified bolus dosage value. For example, the user may review the suggested bolus dosage of 6.2 U depicted in FIG. 1, and may subsequently elect to receive a slightly lower bolus dosage because the user knows that he or she will participate in an extended period of exercise after the proposed meal (thereby offsetting some of the need for a portion of the meal bolus). After receiving the modified bolus dosage amount, the controller device can execute operation 455, which causes the pump device 100 to dispense an amount of insulin to the user that is equivalent to the amount entered in operation 450. As previously described, the bolus dosage can be dispensed over a period of time according to a predetermined profile, such as a ramp profile, a square wave profile, or a curved profile. After the modified bolus dosage is dispensed to the user, the process 400 can then return to operation 405, where the controller device 200 can wait for a subsequent trigger to initiate another suggested bolus dosage calculations.

Revisiting operation 445, if the controller device 200 receives input that indicates the user declined receiving a modified bolus dosage, the process 400 can return to operation 405 and no bolus dosage will be initiated at this time. In some embodiments, the user interface 220 may communicate a warning to the user that the consuming the proposed meal without an insulin bolus dosage may result in negative consequences. In addition or in the alternative, the controller device 200 may start a timer to prompt the user to initiate a bolus dosage at a later time during or immediately after the meal is consumed (e.g., prompt the user to initiate an insulin bolus dosage in 10 minutes, in 15 minutes, in 30 minutes, or the like). When the process 400 returns to operation 405, the controller device 200 can wait for a subsequent trigger to initiate another suggested bolus dosage calculations.

As described in connection with FIG. 11, some embodiments of the infusion pump system 10 include the controller device 200 which can calculate a bolus dosage using information such as data indicative of the user's blood glucose level. In some embodiments, this data can be obtained by the glucose monitoring device 50 and communicated (e.g., by wireless communication) to the controller device 200. In other embodiments, this blood glucose data can be obtained directly by the controller device 200 (e.g., by user input), can be obtained from a blood strip reader device (e.g., via a wired or wireless connection), or can be obtained by a glucose sensor connected to the controller device 200 (e.g., by a wired connection). In these examples, the controller device 200 can store (e.g., in the memory chip 248 depicted in FIG. 9) and later retrieve this blood glucose data for use in a subsequent bolus dosage calculation.

When calculating a bolus dosage, the controller device 200 can incorporate information related to the rate of change in the user's blood glucose level in the suggested bolus calculation. For example, as described in more detail in connection with FIG. 12, a blood glucose level of 160 mg/dL may be within a normal blood glucose range for a user, but a suggested bolus calculation that employs only that glucose level information (without the rate-of-change parameter) might not be indicative of a situation where additional insulin was required. In particular, a rapidly increasing blood glucose level [e.g., 3.0 mg/(dL*min)] can be predictive of a higher blood glucose level in the future. In this example, where a user has a blood glucose level of 160 mg/dL that is rising at a rate of 3.0 mg/(dL*min), if the blood glucose level continues to rise at the same rate, the user's blood glucose level could be over 200 mg/dL in less than 14 minutes. If 200 mg/dL is the upper threshold of the user's normal blood glucose range, the controller device 200 with the suggested bolus features described herein (incorporating the rate of change in the user's blood glucose level in the suggested bolus calculation) can suggest additional insulin nearly 14 minutes prior to the user's blood glucose level exceeding the upper threshold, thereby helping the user to more accurately control his or her blood glucose level.

Figure 12:
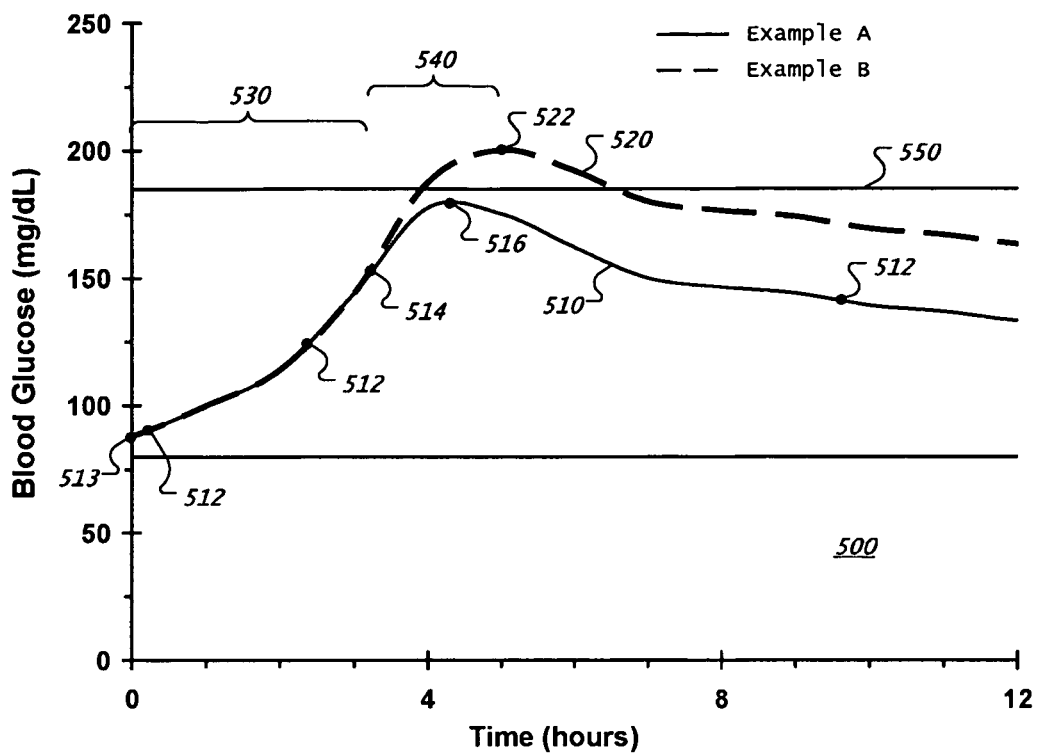
FIGS. 12-13 are diagrams depicting exemplary insulin decay curves, which may be employed in the determination of the rate of change in a user's blood glucose level, in accordance with some embodiments.

Referring now to FIG. 12, a graph 500 depicts a blood glucose curve 510 derived from individual blood glucose measurements 512 (example A) taken from a user of the infusion pump system 10 having the suggested bolus feature described herein. The graph 500 also depicts a theoretical blood glucose curve 520 that illustrates a theoretical blood glucose levels (example B) of the same user utilizing an infusion pump having a bolus calculator that does not account the rate of change in the user's blood glucose level. In region 530 of example A (depicted by curve 510), the user's blood glucose level rises from about 85 mg/dL at time=0 hours (point 513) to about 155 mg/dL at about time=3.25 hours (point 514). In example A, prior to the point 514 (about time=3.25 hours), the user inputs food intake information for a meal that he or she is about to consume, which can trigger the controller device 200 to calculate and suggest a bolus dosage. In this example A, the suggested bolus dosage is calculated to account for the recent rate of change in the user's blood glucose level (previously described in connection with FIG. 11). Thus, when the controller device 200 suggests a bolus dosage, the user's blood glucose level is about 160 mg/dL and rising. FIG. 1 depicts a similar example where the controller device 200 is displaying a suggested bolus dosage of 6.2 units, the user's blood glucose level of 160 mg/dL, an indication that the user's blood glucose is rising, and that the bolus calculation includes a correction factor based on the rate of change in the user's blood glucose level.

Still referring to FIG. 12 and example A, the user can accept the bolus dosage suggested by the controller device 200, which can initiate the delivery of the bolus dosage by the pump device 100, at the point 514. During region 540, the user's blood glucose level continues to rise (e.g., due to the delayed action of the insulin delivered during the bolus dosage, metabolizing the consumed meal, the rate at which the blood glucose level was increasing prior to point 514, and other such factors) until reaching a maximum at point 516 of about 180 mg/dL at about time=4.25 hours. After the point 516, the user's blood glucose level continues to drop due to, for example, the delayed action of the insulin delivered during the bolus dosage, the end of the food intake, a substantially continuous basal rate, and the like. In this example A, shown in graph 500, the user's blood glucose level does not exceed 180 gm/dL.

In the theoretical example B (depicted by the curve 520) shown in FIG. 12, the data points prior to the point 514 (e.g., in the region 530) are equivalent to those used to derive the curve 510. Prior to point 514, the infusion pump in this example calculates a bolus dosage in a manner that is equivalent to the controller device 200 used to calculate the bolus dosage in the previous example, except that the infusion pump in example B does not account for the rate of change in the user's blood glucose level when determining the bolus dosage amount. In this example B, the Blood Glucose Correction Component may be calculated according to: (Current Blood Glucose Level−Target Glucose Level)*Insulin Sensitivity, thereby ignoring the rate of change in the user's blood glucose level. Because the user's blood glucose level is increasing at and before the point 514, the controller device 200 that used the rate of change in the user's blood glucose level when determining the bolus dosage amount in example A suggested a larger bolus dosage than the controller device in example B. Accordingly, the user's blood glucose level in example B (curve 520) increases beyond the upper glucose alarm limit of 185 mg/dL (line 550) and to a greater maximum (e.g., at about point 522) than the blood glucose in level in example A (point 516). In this scenario depicted in FIG. 12, the user benefits from the controller device 200 in example A because it helps to better maintain the user's blood glucose level within a targeted safe range.

Figure 13:
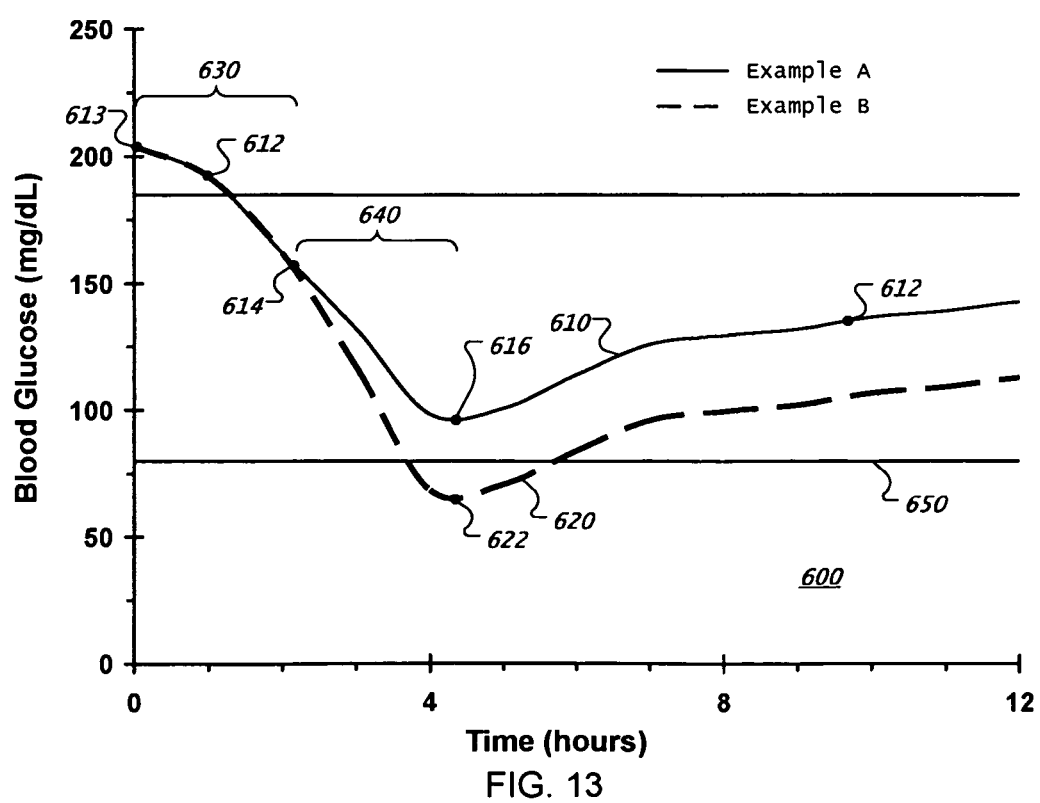

Referring now to FIG. 13, when calculating a suggested bolus dosage for the user, the controller device 200 can incorporate information related to the rate of change in the user's blood glucose level even when the blood glucose level is decreasing. For example, as described in more detail in connection with FIG. 13, a blood glucose level of 160 mg/dL may be within a normal blood glucose range for a user, but a suggested bolus calculation that employs only that glucose level information (without the rate-of-change parameter) might not be indicative of a situation where a lesser amount of insulin was required. In particular, a rapidly decreasing blood glucose level [e.g., −3.0 mg/(dL*min)] can be predictive of a lower blood glucose level in the future. In this example, where a user has a blood glucose level of 160 mg/dL that is falling at a rate of −3.0 mg/(dL*min), for example, due to exercise, if the blood glucose level continues to fall at the same rate, the user's blood glucose level could fall to under 80 mg/dL in less than 27 minutes. If 80 mg/dL is the lower threshold of the user's normal blood glucose range, the controller device 200, with the suggested bolus features described herein (incorporating the rate of change in the user's blood glucose level in the suggested bolus calculation), can suggest a lesser amount of insulin and/or that the user consume additional carbohydrates nearly 14 minutes prior to the user's blood glucose level exceeding the upper threshold, thereby helping the user to more accurately control his or her blood glucose level.

As shown in FIG. 13, a graph 600 depicts a blood glucose curve 610 derived from individual blood glucose measurements 612 (example A) taken from a user of the infusion pump system 10 having the suggested bolus feature described herein. The graph 600 also depicts a theoretical blood glucose curve 620 that illustrates a theoretical blood glucose level (example B) of the same user utilizing an infusion pump having a bolus calculator that does not account the rate of change in the user's blood glucose level. In region 630 of example A (depicted by curve 610), the user's blood glucose level falls from about 205 mg/dL at time=0 hours (point 613) to about 160 mg/dL at about time=2.25 hours (point 614). In example A, prior to the point 614 (about time=2.25 hours), the user inputs food intake information for a meal that he or she is about to consume, which can trigger the controller device 200 to calculate and suggest a bolus dosage. In this example A, the suggested bolus dosage is calculated to account for the recent rate of change in the user's blood glucose level (previously described in connection with FIG. 11). Thus, when the controller device 200 suggests a bolus dosage, the user's blood glucose level is about 160 mg/dL and falling. FIG. 2 depicts a similar example where the controller device 200 is displaying a suggested bolus dosage of 6.2 units, the user's blood glucose level of 160 mg/dL, an indication that the user's blood glucose is falling, and that the bolus calculation includes a correction factor based on the rate of change in the user's blood glucose level.

Still referring to FIG. 13 and example A, the user can accept the bolus dosage suggested by the controller device 200, which can initiate the delivery of the bolus dosage by the pump device 100, at the point 614. During region 640, the user's blood glucose level continues to fall (e.g., due to the delayed action of the insulin delivered during the bolus dosage, the effect of exercise, a substantially continuous basal rate, the rate at which the blood glucose level was decreasing prior to point 614, and other such factors) until reaching a minimum at point 616 of about 95 mg/dL at about time=4.25 hours. After the point 616, the user's blood glucose level begins to rise due to, for example, the delayed action of the previously consumed meal, the cessation of exercise, and the like. In this example A shown in graph 600, the user's blood glucose level does not fall below exceed 80 gm/dL.

In the theoretical example B (depicted by the curve 620) shown in FIG. 13, the data points prior to the point 614 (e.g., in the region 630) are equivalent to those used to derive the curve 610. Prior to point 614, the infusion pump in this example calculates a bolus dosage in a manner that is equivalent to the controller device 200 used to calculate the bolus dosage in the previous example, except that the infusion pump in example B does not account for the rate of change in the user's blood glucose level when determining the bolus dosage amount. In this example B, the Blood Glucose Correction Component may be calculated according to: (Current Blood Glucose Level−Target Glucose Level)*Insulin Sensitivity, thereby ignoring the rate of change in the user's blood glucose level. Because the user's blood glucose level is decreasing at and before the point 614, the controller device 200 that used the rate of change in the user's blood glucose level when determining the bolus dosage amount in example A suggested a smaller bolus dosage than the controller device in example B. Accordingly, the user's blood glucose level in example B (curve 620) decreased beyond the lower glucose alarm limit of 80 mg/dL (line 650) and to a lesser minimum (e.g., at about point 622) than the blood glucose in level in example A (point 616). In this scenario depicted in FIG. 13, the user benefits from the controller device 200 in example A because it helps to better maintain the user's blood glucose level within a targeted safe range.

Figure 14:
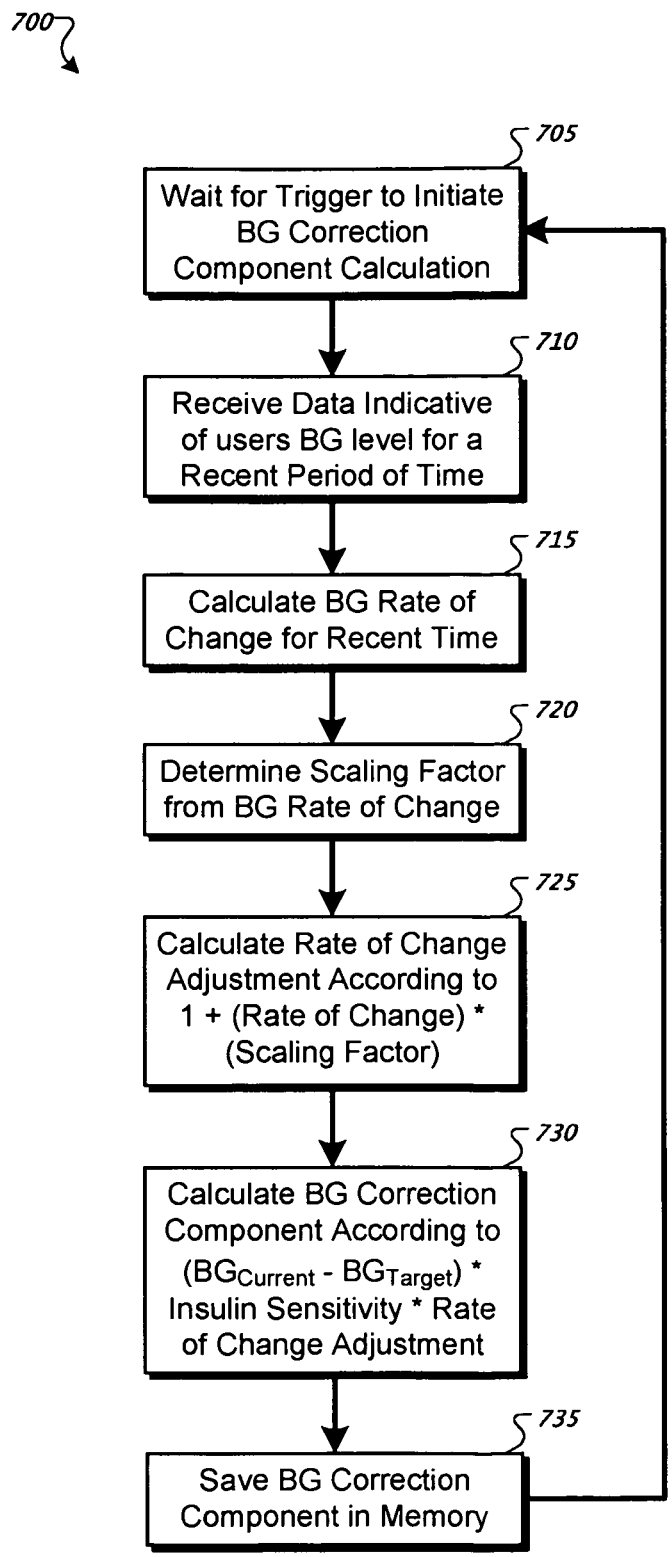
FIGS. 14-16 are flow diagrams depicting exemplary processes used to determine the blood glucose correction component of a bolus dosage of insulin in response to, in part, the rate of change in a user's blood glucose level, in some embodiments.
Figure 15:
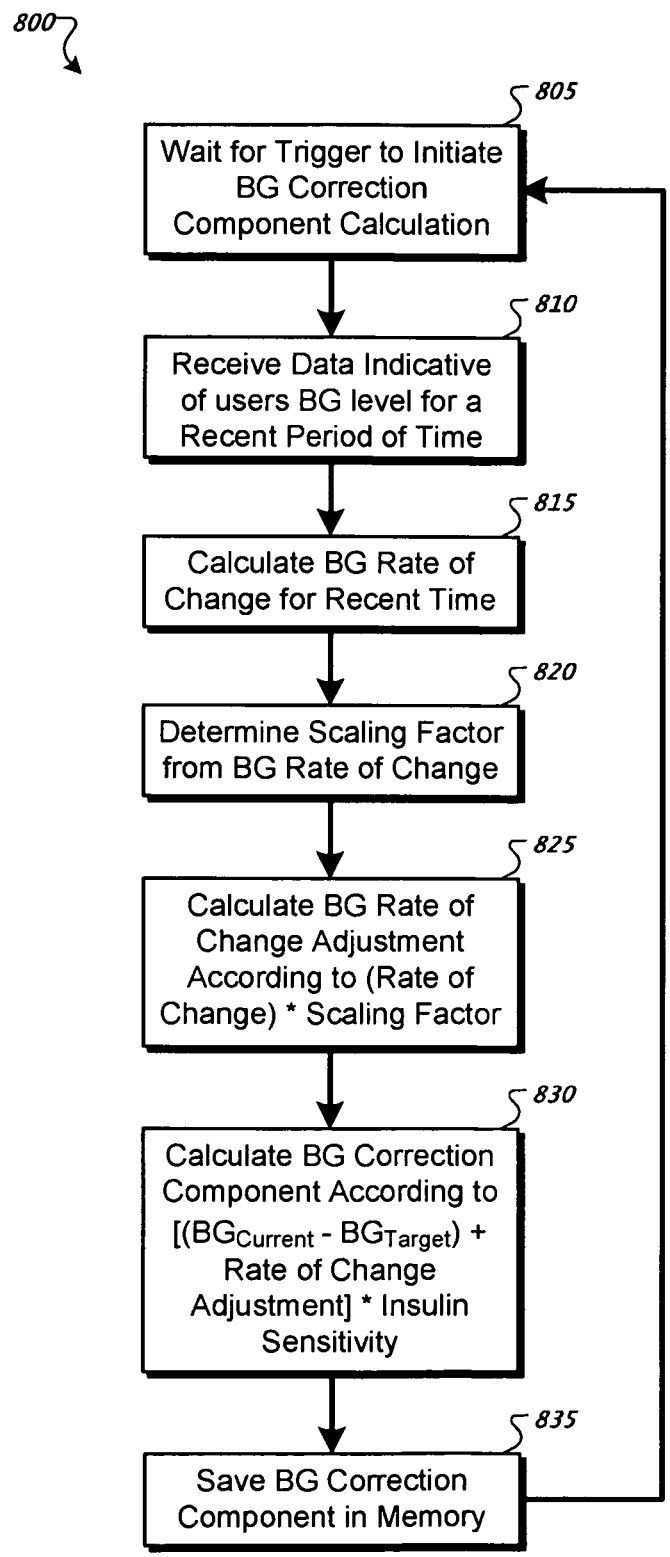
Figure 16:
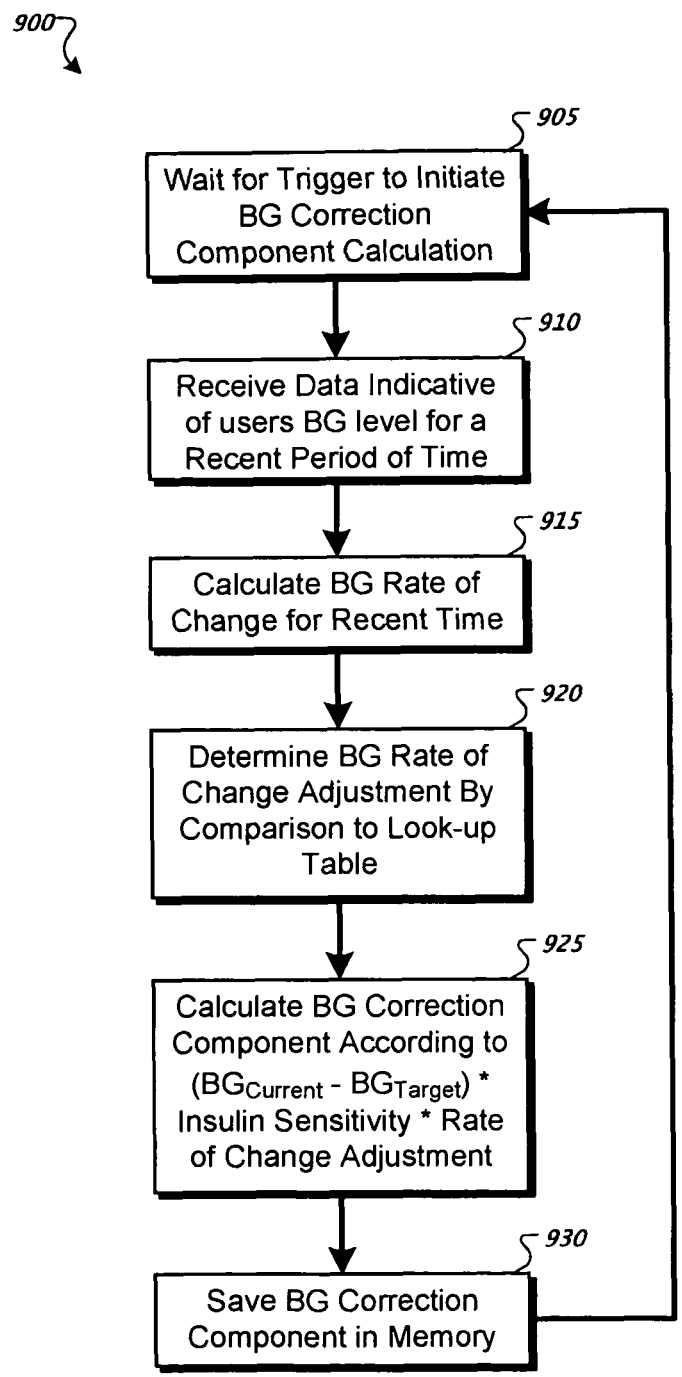

Referring now to FIGS. 14-16, the controller device 200 can use information related to the rate of change in a user's blood glucose level when calculating a bolus dosage. For example, when a bolus dosage calculation is triggered, the controller device 200 can calculate a suggested bolus dosage of insulin as previously described in connection with FIG. 11. The blood glucose rate-of-change parameter used in such a bolus calculation can be calculated from the user's blood glucose information stored in the memory (e.g., the memory chip 248 depicted in FIG. 9) of the controller device 200. One exemplary method of calculating the rate of change includes taking the difference between the blood glucose level associated with a latest blood glucose measurement and one level associated with a measurement prior to the latest. Dividing this value by the time elapsed between the two measurements yields a value that can be used as the rate of change in the user's blood glucose level. There are other ways of calculating the user's blood glucose rate of change that will work with a bolus dosage calculation performed by the controller device 200. For example, another method of calculating the rate-of-change parameter includes averaging the rate of change associated with the most recent blood glucose measurement and the pervious rate of change associated with a measurement prior to the most recent. In such circumstances, the rate-of-change parameter is based upon a broader range of recent blood glucose data points. Once the rate-of-change parameter is determined, there exists different ways to use this information to account for the rate of change in the user's blood glucose level in the bolus dosage calculation, examples of which are described in connection with FIGS. 14-16.

Referring now to FIG. 14, an illustrative process 700 for determining a blood glucose correction component, that includes the use of blood glucose rate of change information, can include a number of operations performed by the controller device 200. In some embodiments, the controller device 200 can initiate a bolus dosage calculation, such as described in connection with FIG. 11. Some or all of the operations in this process 700 may be incorporated into the steps 415 or 425 (FIG. 11) so as to provide a suggested bolus dosage to the user. The bolus dosage calculation can include a blood glucose correction component that incorporates the user's blood glucose rate of change information. In operation 705, the controller device 200 can initiate the calculation of a blood glucose correction component (e.g., for use in a bolus dosage calculation). In operation 710, the controller device 200 can receive data indicative of a user's blood glucose level for a recent period of time, including a most recent blood glucose measurement. For example, the controller device 200 can retrieve two blood glucose level values, representing the information for the two most recent blood measurements, from memory (e.g., the memory chip 248 depicted in FIG. 9). In another example, the controller device 200 can retrieve one or more recent blood glucose levels stored in memory and can initiate a current blood glucose measurement (e.g., by receiving information from the glucose monitoring device 50, by instructing the user to perform a blood glucose measurement and input the data into the controller device 200, by inserting a glucose test strip containing a blood sample into a strip reader device that communicates with the controller device 200, or the like). In yet another example, the controller device 200 can retrieve blood glucose information for a period of time (e.g., less than one hour, less than 30 minutes, about 2 minutes to about 20 minutes, and about 5 minutes to about 15 minutes) for use in the calculation of the blood glucose correction component.

In some embodiments, the controller device 200 can execute operation 715 to calculate the blood glucose rate of change for the most recent time. For example, the controller device 200 can subtract the blood glucose level corresponding to a previous measurement from the most recent measurement and divide this value by the change in time between the two measurements. In another example, three or more recent blood glucose measurements can be used provide a broader range of data points for the calculated rate-of-change parameter (e.g., in an effort to reduce the effect of any noise in the signal from the glucose monitoring device 50). In another example, the controller device 200 can estimate the instantaneous blood glucose rate of change at a time (e.g., the most current measurement) from a blood glucose curve, such as the one found in FIG. 12.

As an alternative to operations 710-715, one or more of these operations can be performed by an external blood glucose meter (e.g., a blood strip reader or the like), the results of which can be transferred to the controller device 200. For example, the user can make multiple blood glucose measurements over a period of time using a blood strip reader. These blood glucose measurements can be stored by the strip reader (or another device) and later used to determine a current rate of change in the user's blood glucose level. This rate of change information can be manually input by the user into the controller device 200, via the user interface 220, and used in subsequent operations by the controller device 200. Alternatively, this rate of change information can be wirelessly communicated from the blood glucose meter to the controller device 200.

Still referring to the embodiment in FIG. 14, after calculating a blood glucose rate-of-change parameter, the process 700 can execute operation 720 and determine a rate of change scaling factor for use in the scaled rate of change adjustment described below. In some embodiments, the rate of change value determined in 715 may be scaled in a blood glucose correction component calculation. For example, in some users, the calculated rate-of-change parameter may vary between about −3 mg/(dL*min) and about +3 mg/(dL*min). In this example, the rate of change value can be multiplied by a fixed scaling factor of 0.10 (dL*min)/mg to scale the rate of change to between about −0.3 and about +0.3. In other embodiments, the scaling factor used can be selected from multiple possibilities based, at least in part, on the rate of change value. For example, the process 700 may employ different scaling factors for positive and negative rate-of-change values:

for rate-of-change values greater than 0 mg/dL/min, scaling factor=0.2
    for rate-of-change values less than 0 mg/dL/min, scaling factor=0.1

In another example, the process 700 may employ different scaling factors based on the magnitude of the rate of change value:

for rate-of-change values from 0 to 1.0 mg/dL/min, scaling factor=0
    for rate-of-change values greater than 1.0 to 2.0 mg/dL/min, scaling factor=0.1
    for rate-of-change values greater than 2.0 to 3.0 mg/dL/min, scaling factor=0.2

In some embodiments, a maximum and/or minimum value can be enforced on the rate-of-change value. For example, if the rate-of-change value exceeds magnitude of 3.0, the controller device 200 can use a scaling factor that, when multiplied by the rate of change value, yields +0.3 for positive rate-of-change values and −0.3 for negative rate-of-change values.

Still referring to FIG. 14, the controller device 200 can execute operation 725 and calculate a rate of change adjustment (e.g., for use in the calculation of a bolus dosage). This rate of change adjustment can be based, at least in part, on data indicative of a user's blood glucose level. In operation 725, the controller device 200 can calculate the rate of change adjustment as follows:

Rate of Change Adjustment=[1+(Rate of Change*Scaling Factor$_{roc}$)], where Rate of Change in mg/(dL*min) represents the recent rate of change in the user's blood glucose level, and Scaling Factor$_{roc}$ in (dL*min)/mg represents a scaling factor (e.g., stored in the controller device 200) that can be used to scale the Rate of Change value.

In some embodiments, the controller device 200 can use the most recent blood glucose level data received from the monitoring device 50 for use in rate-of-change calculations. In another example, the controller device 200 may receive data points indicative of the user's blood glucose levels over a recent period of time during operation 710 (e.g., from the glucose monitoring device 50), and may receive data indicative of the user's current blood glucose level from a second source, such as an external blood glucose meter (e.g., a blood strip reader or the like). This blood glucose data from the external blood glucose meter may be manually input to the controller device 200 by the user or may be wirelessly communicated from the blood glucose meter. It should be understood from the description herein that the user's blood glucose level data (e.g., the current blood glucose level value used to calculate the blood glucose correction component in operation 730) need not come from the same source as the data used to determine the user's blood glucose rate of change.

The controller device 200 can execute operation 730 to calculate the blood glucose correction component based, at least in part, on the rate of change adjustment calculated in operation 725. In operation 730, the controller device 200 can calculate the blood glucose correction component as follows:

Blood Glucose Correction Component=(Current Blood Glucose Level−Target Glucose Level) *Insulin Sensitivity*Rate of Change Adjustment, where the Current Blood Glucose Level represents the most recent blood glucose level, the Target Glucose Level represents the user's desired blood glucose level, Insulin Sensitivity represents a user specific value that correlates the number of units of insulin required to alter the user's blood glucose level by 1 mg/dL, the Rate of Change Adjustment (unitless) is a scaled value based in part on the rate of change in the user's blood glucose level, and.

It should be understood from the description herein that the Rate of Change Adjustment (operation 725) can be contemporaneously calculated with the Blood Glucose Correction Component (operation 730) or, alternatively, these operations 725 and 730 can be processed in discrete steps.

In operation 735, the blood glucose correction component can be saved to memory where it can be retrieved, for example, to be used in a bolus dosage calculation such as that which was described previously in connection with FIG. 11. After completion of operation 735, the process 700 can return to operation 705 and wait for a future blood glucose correction component calculation to be initiated.

In some embodiments, such as the one described in connection with FIG. 14, a blood glucose correction component can include a rate of change adjustment that is multiplied by the difference in the user's current and the target blood glucose levels, thus causing the effect of the rate of change adjustment to change based on the size of this difference. In an alternate embodiment, such as the one described below in connection with FIG. 15, a rate of change adjustment is calculated and added to the blood glucose difference, thus causing the effect of the rate of change adjustment to be independent of the calculated difference in blood glucose values.

Referring now to FIG. 15, an illustrative process 800 for determining the blood glucose correction component to calculate a suggest bolus dosage can include a number of operations performed by the controller device 200. In some embodiments, the controller device 200 can initiate a bolus dosage calculation, such as described in connection with FIG. 11. Some or all of the operations in this process 800 may be incorporated into the steps 415 or 425 (FIG. 11) so as to provide a suggested bolus dosage to the user. The bolus dosage calculation can include a blood glucose correction component that incorporates information related to the rate at which the user's blood glucose level is changing. In operation 805, the controller device 200 can initiate the calculation of a blood glucose correction component. In operation 810, the controller device 200 can receive data indicative of a user's blood glucose level for a recent period of time, including a most recent blood glucose measurement. For example, the controller device 200 can retrieve one or more recent blood glucose levels stored in memory and can optionally initiate a current blood glucose measurement.

In some embodiments, the controller device 200 can execute operation 815 to calculate the blood glucose rate of change for the most recent time. For example, the controller device 200 can subtract the blood glucose level corresponding to a previous measurement from the most recent measurement and divide this value by the change in time between the two measurements. In another example, three or more recent blood glucose measurements can be used provide a broader range of data points for the calculated rate-of-change parameter (e.g., in an effort to reduce the effect of any noise in the signal from the glucose monitoring device 50). In further example, the controller device 200 can estimate the instantaneous blood glucose rate of change at a time (e.g., the most current measurement) from a blood glucose curve, such as curve 610 found in FIG. 13.

As an alternative to operations 810-815, one or more of these operations can be performed by an external blood glucose meter (e.g., a blood strip reader or the like), the results of which can be transferred to the controller device 200. For example, the user can make multiple blood glucose measurements over a period of time using a blood strip reader. These blood glucose measurements can be stored by the strip reader (or another device) and later used to determine a current rate of change in the user's blood glucose level. This rate of change information can be manually input by the user into the controller device 200, via the user interface 220, and used in subsequent operations by the controller device 200. Alternatively, this rate of change information can be wirelessly communicated from the blood glucose meter to the controller device 200.

Still referring to the embodiment in FIG. 15, after calculating a blood glucose rate of change, the process 800 can execute operation 820 and determine a rate of change scaling factor for use in the rate of change adjustment calculation described below. In some embodiments, the rate of change value determined in 815 may be scaled in a rate of change adjustment calculation. For example, in some users, the calculated rate-of-change parameter may vary between about −3 mg/(dL*min) and about +3 mg/(dL*min)In some embodiments, a fixed scaling factor of 4.0 min can be used to scale the rate of change to between about −12.0 mg/dL and about +12.0 mg/dL. In other embodiments, the scaling factor used can be selected from multiple possibilities based, at least in part, on the rate of change value. For example, different scaling factors can be used for positive and negative rate of change values. Different scaling factors may also be employed based on the magnitude of the rate of change value. In some embodiments, a maximum and/or minimum value can be enforced on the rate of change adjustment value. For example, if the rate-of-change value exceeds magnitude of 3.0, the controller device 200 can use a scaling factor that, when multiplied by the rate-of-change value, yields +12.0 mg/dL for positive rate-of-change values and −12.0 mg/dL for negative rate-of-change values.

In some embodiments, the controller device 200 can execute operation 825 and calculate a rate of change adjustment based, at least in part, on data indicative of a user's blood glucose level. In operation 825 of this embodiment, the controller device 200 can calculate the rate of change adjustment as follows:

Rate of Change Adjustment=(Rate of Change*Scaling Factor$_{roc}$), where Rate of Change in mg/(dL*min) represents the current rate of change in the user's blood glucose level, and Scaling Factor$_{roc}$, in units of minutes, represents a scaling factor (e.g., stored in the controller device 200) that can be used to scale the Rate of Change value.

In some embodiments, the controller device 200 can use the most recent blood glucose level data received from the monitoring device 50 for use in rate-of-change calculations. In another example, the controller device 200 may receive data points indicative of the user's blood glucose levels over a recent period of time during operation 810 (e.g., from the glucose monitoring device 50), and may receive data indicative of the user's current blood glucose level from a second source, such as an external blood glucose meter (e.g., a blood strip reader or the like). This blood glucose data from the external blood glucose meter may be manually input to the controller device 200 by the user or may be wirelessly communicated from the blood glucose meter. It should be understood from the description herein that the user's blood glucose level data (e.g., the current blood glucose level value used to calculate the blood glucose correction component in operation 830) need not come from the same source as the data used to determine the user's blood glucose rate of change.

Still referring to FIG. 15, the controller device 200 can execute operation 830 and calculate the blood glucose correction component based, at least in part, on the rate of change adjustment calculated in operation 825. In operation 830, the controller device 200 can calculate the blood glucose correction component as follows:

Blood Glucose Correction Component=[(Current Blood Glucose Level−Target Glucose Level)+Rate of Change Adjustment]*Insulin Sensitivity, where the Current Blood Glucose Level represents the most recent blood glucose level, the Target Glucose Level represents the user's desired blood glucose level, the Rate of Change Adjustment is a scaled value based in part on the rate of change in the user's blood glucose level, and Insulin Sensitivity represents a user specific value that correlates the number of units of insulin required to alter the user's blood glucose level by 1 mg/dL.

It should be understood from the description herein that the Rate of Change Adjustment (operation 825) can be contemporaneously calculated with the Blood Glucose Correction Component (operation 830) or, alternatively, these operations 825 and 830 can be processed in discrete steps.

In operation 835, the blood glucose correction component can be saved to memory (e.g., the memory chip 248 depicted in FIG. 9) where it can be retrieved, for example, to be used in a bolus dosage calculation such as that which was described previously. After completion of operation 835, the process 800 can return to operation 805 and wait for a future blood glucose correction component calculation to be initiated.

Referring now to FIG. 16, in an alternate embodiment, a rate of change adjustment (e.g., that is to be used in a bolus dosage calculation) can be determined by comparing a rate-of-change parameter to a look-up table, which can indicate a predetermined rate-of-change adjustment value that corresponds to the given parameter. An illustrative process 900 for determining a blood glucose correction component (e.g., for a suggested bolus dosage calculation) can account for the user's blood glucose rate of change information. In some embodiments, the controller device 200 can initiate a bolus dosage calculation, such as described in connection with FIG. 11. Some or all of the operations in this process 900 may be incorporated into the steps 415 or 425 (FIG. 11) so as to provide a suggested bolus dosage to the user. The bolus dosage calculation can include a blood glucose correction component that incorporates the user's blood glucose rate of change information. In operation 905, the controller device 200 can initiate the calculation of a blood glucose correction component. In operation 910, the controller device 200 can receive data indicative of a user's blood glucose level for a recent period of time, including a most recent blood glucose measurement. For example, the controller device 200 can retrieve blood glucose information for a period of time (e.g., two less than one hour, less than 30 minutes, about 2 minutes to about 20 minutes, and about 5 minutes to about 15 minutes) for use in the calculation of the blood glucose correction component.

In some embodiments, the controller device 200 can execute operation 915 to calculate the blood glucose rate-of-change parameter for a recent time. For example, the controller device 200 can subtract the blood glucose level corresponding to a previous blood glucose measurement from the blood glucose level corresponding to a more recent measurement and divide this value by the change in time between the two measurements. In another example, three or more recent blood glucose measurements can be used provide a broader range of data points for the calculated rate-of-change parameter (e.g., in an effort to reduce the effect of any noise in the signal from the glucose monitoring device 50).

As an alternative to operations 910-915, one or more of these operations can be performed by an external blood glucose meter (e.g., a blood strip reader or the like), the results of which can be transferred to the controller device 200. For example, the user can make multiple blood glucose measurements over a period of time using a blood strip reader. These blood glucose measurements can be stored by the strip reader (or another device) and later used to determine a current rate of change in the user's blood glucose level. This rate of change information can be manually input by the user into the controller device 200, via the user interface 220, and used in subsequent operations by the controller device 200. Alternatively, this rate of change information can be wirelessly communicated from the blood glucose meter to the controller device 200.

Still referring to FIG. 16, the controller device 200 can execute operation 920 to determine a rate of change adjustment based, at least in part, on data indicative of a user's blood glucose information. In operation 920, the controller device 200 can compare the rate-of-change parameter determined in operation 915 to a look-up table to determine a rate of change adjustment. For example, the look-up table may provide different rate of change adjustments based upon the rate-of-change parameter as follows:

for rate-of-change values less than −3.0 mg/dL/min,
   Rate of Change Adjustment=0.7
for rate-of-change values less than −2.0 to −3.0 mg/dL/min,
   Rate of Change Adjustment=0.9
for rate-of-change values less than 0 to −2.0 mg/dL/min,
   Rate of Change Adjustment=1.0
for rate-of-change values from 0 to 1.0 mg/dL/min,
   Rate of Change Adjustment=1.0
for rate-of-change values greater than 1.0 to 2.0 mg/dL/min,
   Rate of Change Adjustment=1.1
for rate-of-change values greater than 2.0 to 3.0 mg/dL/min,
   Rate of Change Adjustment=1.2
for rate-of-change values greater than 3.0 mg/dL/min,
   Rate of Change Adjustment=1.3

In some embodiments, the controller device 200 can use the most recent blood glucose level data received from the monitoring device 50 for use in rate-of-change calculations. In another example, the controller device 200 may receive data points indicative of the user's blood glucose levels over a recent period of time during operation 910 (e.g., from the glucose monitoring device 50), and may receive data indicative of the user's current blood glucose level from a second source, such as an external blood glucose meter (e.g., a blood strip reader or the like). This blood glucose data from the external blood glucose meter may be manually input to the controller device 200 by the user or may be wirelessly communicated from the blood glucose meter. It should be understood from the description herein that the user's blood glucose level data (e.g., the current blood glucose level value used to calculate the blood glucose correction component in operation 925) need not come from the same source as the data used to determine the user's blood glucose rate of change.

In operation 925, the controller device 200 can calculate the blood glucose correction component based, at least in part, on the rate of change adjustment determined in operation 920. In operation 925, the controller device 200 can calculate the blood glucose correction component as follows:

> Blood Glucose Correction Component=(Current Blood Glucose Level−Target Glucose Level) *Rate of Change Adjustment*Insulin Sensitivity, where the Current Blood Glucose Level represents the most recent blood glucose level, the Target Glucose Level represents the user's desired blood glucose level, the Rate of Change Adjustment (unitless) is a scaled value based in part on the rate of change in the user's blood glucose level, and Insulin Sensitivity represents a user specific value that correlates the number of units of insulin required to alter the user's blood glucose level by 1 mg/dL.

Still referring to FIG. 16, in operation 930, the blood glucose correction component can be saved to memory where it can be retrieved, for example, to be used in a bolus dosage calculation such as that which was described previously in connection with FIG. 11. After completion of operation 930, the process 900 can return to operation 905 and wait for a future blood glucose correction component calculation to be initiated.

Figure 17:
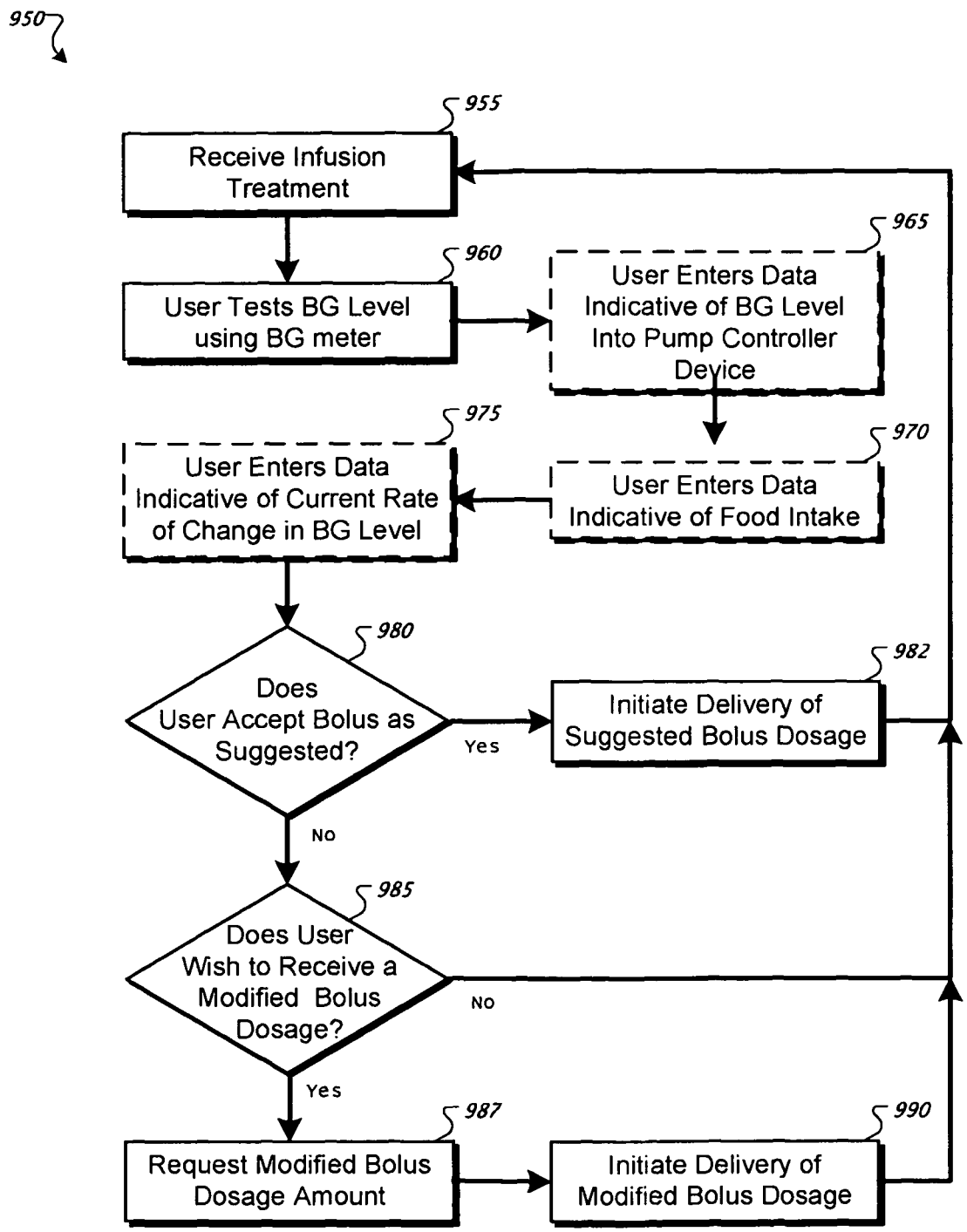
FIG. 17 is a flow diagram depicting an exemplary process of prompting a suggested bolus dosage, in accordance with some embodiments.

Referring now to FIG. 17, in one exemplary process 950, a user can prompt a suggested bolus calculation by testing his or her blood glucose level using an external blood glucose meter. In operation 955, the user can receive infusion treatment as the pump assembly 60 operates to deliver insulin by basal dosages, selected bolus dosages, or a combination thereof. In operation 960, the user can test his or her blood glucose level using a blood glucose meter (e.g., a blood strip reader device or the like). For example, the user can test his or her blood glucose level with a blood strip reader in response to prompting by the controller device 200. In another example, the user can test his or her blood glucose level before consuming a meal.

In operation 965, the user can optionally enter the blood glucose level determined during operation 960 into the pump controller device 200 via the user interface 220. For example, the user may read the blood glucose test results from the blood glucose meter display, and then input this information into the controller device 200. In alternate embodiments, the blood glucose level information determined during operation 960 can be transmitted (either wirelessly or in a wired manner) to the pump controller device 200, possibly eliminating the need for the user to manually enter the information. In operation 970, the user can optionally enter data indicative of food intake (e.g., a meal that is about to be consumed, a meal that has recently been consumed, or the like). For example, if the user is testing his or her blood glucose level before consuming a meal, the user may input such food intake information when inputting the blood glucose level.

Optionally, the user may manually enter the rate-of-change information for his or her blood glucose level (rather than this information being generated from the data received from the monitoring device 50). In these circumstances, optional operation 975 may be implemented so that the user can enter data indicative of the current rate of change in the user's blood glucose level into the controller device 200. For example, when using a blood glucose meter, the blood glucose meter may store blood glucose measurements performed by the user, which can be used to determine the rate of change in the user's blood glucose level. When prompted by the controller device 200, the user may enter the most recent rate of change data into the pump controller device 200.

After the user's current blood glucose information is input into the controller device 200, the controller device 200 may be prompted to calculate a suggested bolus dosage as previously described herein. In operation 980, the user can choose to accept or decline a bolus dosage that is suggested (e.g., via the display 222 of the controller device 200) by the controller device 200. For example, the user can choose to accept the bolus dosage amount by pressing button 224a or decline the bolus dosage amount, as suggested, by pressing button 224d. If the user chooses to accept the bolus amount as suggested, the user can initiate delivery of this bolus amount during operation 982. If the user chooses to decline the bolus dosage as suggested, the user may elect to modify the bolus dosage amount (operation 985). For example, the user can choose to modify the bolus dosage amount by pressing button 224a or decline the bolus dosage altogether by pressing button 224d. If the user chooses to decline the bolus dosage altogether, the process 950 can return to operation 955 where the user returns to receiving normal medical treatment (e.g., a basal infusion rate) by the infusion pump system 10.

During operation 985, if the user chooses (e.g., by pressing button 224d) to modify the bolus dosage amount, the user may, during operation 987, enter a modified bolus dosage amount. In operation 990, the modified bolus dosage amount can be received by the user, after which the process 950 can return to operation 905. It should be understood that the infusion pump system 10 can perform additional steps between operation 987 and 990 to ensure the safety of the user. For example, the controller device 200 can verify that the bolus dosage amount suggested by the user during operation 987 is within an acceptable range of values. In another example, the controller device 200 can prompt the user to accept the modified bolus dosage amount or enter another bolus dosage amount.

As previously described in connection with FIGS. 1-2, the controller device 200 that provides the suggested bolus dosage to the user may be configured as a reusable device that communicates with a disposable pump device 100 to controllably dispense the dosages of medicine. It should be understood from the description herein that, in alternative embodiments, the controller device to provide the suggested bolus dosage can be configured as a single unit in which the control components and the pump drive system are arranged in a single housing. In these alternative embodiments, the pump assembly (including the controller device and the pump device) may have a different size and shape and may operate as a reusable unit that can communicate with a number of monitoring devices 50 over a period of time (refer, for example, to embodiments depicted in FIGS. 18-19). In such circumstances, the controller device can be configured to provide a suggested bolus dosage in a manner that accounts for the recent rate of change to the user's blood glucose level. For example, the controller device can be configured to provide a suggested bolus dosage according to one or more of the processes described in connection with FIGS. 11-16.

Referring to the examples depicted in FIGS. 18-19, some embodiments of a portable infusion pump system 1000 (or 1100) can employ a reusable pump assembly 1010 (or 1110) rather than a disposable pump device 100 as previously described in connection with FIGS. 1-2. In such circumstances, the reusable pump assembly 1010 (or 1110) can include control circuitry 1040 (or 1140) that receives blood glucose information from a glucose monitoring device 50 and that controls a drive mechanism to dispense insulin or another medication from an infusion set 70. Similar to previously described embodiments, the control circuitry 1040 (or 1140) can calculate and suggest bolus dosages based on, for example, food intake data indicative of meals that the user consumes, information derived from blood glucose data including the recent rate of change to the user's blood glucose levels), previously delivered insulin dosages, and other factors. Accordingly, the reusable infusion pump system (e.g., the pump system 1000, the pump system 1100, or the like) can be configured to more precisely control the user's blood glucose level as illustrated (for example) in connection with FIGS. 12-13.

Figure 18:
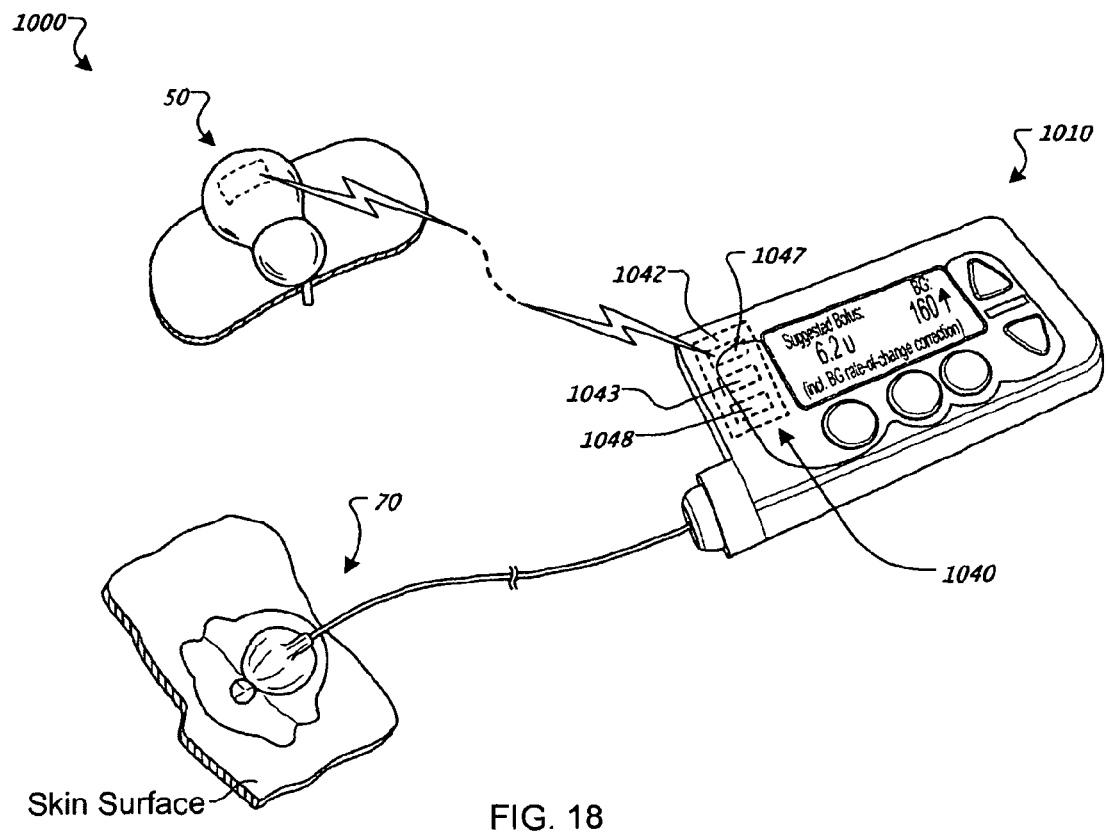
FIG. 18 is a perspective view of another pump system configured to deliver medicine to a user and to calculate bolus dosages of insulin in response to, in part, the rate of change in a user's blood glucose level, in accordance with certain embodiments.

In the embodiment depicted in FIG. 18, the pump system 1000 can include the glucose monitoring device 50 in communication with the infusion pump assembly 1010 for the purpose of supplying data indicative of a user's blood glucose level to the control circuitry 1040 (via a wireless connection in this embodiment). The infusion control circuitry 1040 can utilize the data indicative of a user's blood glucose level in the calculation of a suggested bolus dosage. For example, the pump system 1000 can calculate the recent rate of change in the user's blood glucose level and can use this information as part of the calculation of a suggested bolus dosage.

Similar to previously described embodiments, the pump assembly 1010 can include a housing structure that defines a cavity in which a medicine cartridge can be received. For example, the infusion pump assembly 1010 can be adapted to receive a medicine cartridge in the form of a carpule that is preloaded with insulin or another medicine (not shown in FIG. 18; refer for example to cartridge 120 in FIG. 2). The pump drive system can act upon the fluid cartridge to controllably dispense medicine through the infusion set 70 and into the user's tissue or vasculature. In this embodiment, the user can wear the pump assembly 1010 on the user's skin under clothing or in the user's pocket while receiving the medicine dispensed through the infusion set 70. The pump assembly 1010 includes a user interface having a display screen and a number of user-actuatable buttons so that the user can interact with pump assembly 1010 and input data or commands.

Still referring to FIG. 18, the infusion the control circuitry 1040 can include a main processor board 1042 that is in communication with a power supply (not shown). The main processor board 1042 can include one or more processors 1043, a communication device 1047, and at least one memory chip 1048. Similar to previously described embodiments, the control circuitry 1040 can wirelessly receive information indicative of a user's blood glucose level from the glucose monitoring device 50 via the communication device 1047. This information can be stored in the memory chip 1048 for retrieval at a later time. Similar to previously described embodiments, the processors 1043 can be used to calculate a suggested bolus dosage in response to, for example, a high blood glucose level, a rapidly rising blood glucose level, recently entered meal information, or the like. The infusion pump assembly 1010 may perform one or more of the exemplary processes for the calculation of a suggested bolus dosage as previously described in connection with FIGS. 11 and 14-16.

Figure 19:
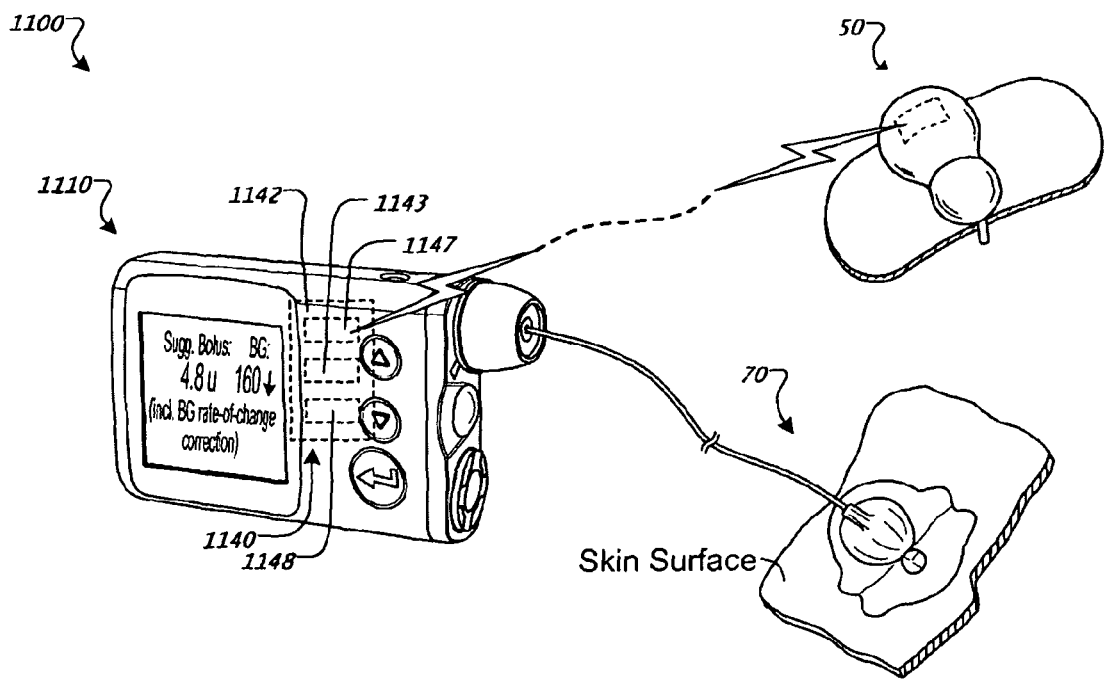
FIG. 19 is a perspective view of yet another pump system configured to deliver medicine to a user and to calculate bolus dosages of insulin in response to, in part, the rate of change in a user's blood glucose level, in accordance with certain embodiments.

Referring now to FIG. 19, the pump system 1100 can include the glucose monitoring device 50 in communication with the infusion pump assembly 1110 for the purpose of supplying data indicative of a user's blood glucose level to the control circuitry 1140 (via a wireless connection in this embodiment). The infusion control circuitry 1140 can utilize the data indicative of a user's blood glucose level, for example, in the calculation of a suggested bolus dosage. For example, the pump system 1100 can calculate the recent rate of change in the user's blood glucose level and can use this information as part of the calculation of a suggested bolus dosage.

Similar to previously described embodiments, the pump system 1110 can include a housing structure that defines a cavity in which a medicine cartridge can be received. For example, the infusion pump assembly 1110 can be adapted to receive a medicine cartridge in the form of a carpule that is preloaded with insulin or another medicine (not shown in FIG. 19; refer for example to cartridge 120 in FIG. 2). The pump drive system can act upon the fluid cartridge to controllably dispense medicine through the infusion set 70 and into the user's tissue or vasculature. In this embodiment, the user can wear the pump assembly 1110 on the user's skin under clothing or in the user's pocket while receiving the medicine dispensed through the infusion set 70. The pump assembly 1010 includes a user interface having a display screen and a number of user-actuatable buttons so that the user can interact with pump assembly 1010 and input data or commands.

Still referring to FIG. 19, the infusion the control circuitry 1140 can include a main processor board 1142 that is in communication with a power supply (not shown). The main processor board 1142 can include one or more processors 1143, a communication device 1147, and at least one memory chip 1148. Similar to previously described embodiments, the control circuitry 1140 can wirelessly receive information indicative of a user's blood glucose level from the glucose monitoring device 50 via the communication device 1147. This information can be stored in the memory chip 1148 for retrieval at a later time. Similar to previously described embodiments, the processors 1143 can be used to calculate a bolus dosage in response to, for example, a high blood glucose level, a rapidly rising blood glucose level, recently entered meal information, or the like. The infusion pump assembly 1010 may perform one or more of the exemplary processes for the calculation of a suggested bolus dosage as previously described in connection with FIGS. 11 and 14-16. In such circumstances, the infusion pump assembly 1010 can calculate the recent rate of change in the user's blood glucose level and can use this rate-of-change information as a parameter in the calculation of a suggested bolus dosage for the user. In doing so, the user may benefit from the suggested bolus feature of the infusion pump assembly 1010 because it helps to maintain the user's blood glucose level within a targeted safe range.

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
   a portable pump housing that receives insulin for dispensation to a user, the pump housing at least partially containing a pump drive system to dispense the insulin through a flow path to the user;
   a controller that communicates with the pump drive system to dispense the insulin from the portable pump housing; and
   a monitoring device that communicates glucose information to the controller, the glucose information being indicative of a blood glucose level of the user,
   wherein the controller displays a suggested bolus dosage in response to user input, the suggested bolus dosage being at least partially dependent upon both the blood glucose level of the user and a rate of change to the blood glucose level of the user,
   wherein the controller determines the suggested bolus dosage based on the blood glucose level of the user, a rate of change to the blood glucose level of the user, user input of food intake information, and an estimate of an amount of insulin already delivered to the user which has not yet acted on the user, wherein the controller device determines the suggested bolus dosage in response to user input of food intake information, wherein the controller determines the suggested bolus dosage according to the function:

Suggested Bolus Dosage=(Food Offsetting Component)+(Blood Glucose Correction Component)−(Insulin Load Correction Component), and wherein the controller determines the Blood Glucose Correction Component according to the function:

Blood Glucose Correction Component=(Current Blood Glucose Level−Target Glucose Level) * (Insulin Sensitivity) * [1+(Rate of Change * Scaling Factor)], where Rate of Change represents a recent rate of change in the user's blood glucose level.

2. The system of claim 1, wherein the monitoring device comprises: a portable housing wearable on the user's skin, a sensor shaft that penetrates into the user's skin, and a wireless communication device housed in the portable housing and configured to transmit the glucose information to said wireless communication device of the controller device.

3. The system of claim 1, wherein the portable pump housing is configured to receive an insulin cartridge and a cap device that is attachable to the pump housing so as to seal the space after receiving the insulin cartridge, the cap device comprising a fluid flow path extending therethrough.

4. The system of claim 3, further comprising the insulin cartridge, said insulin cartridge comprising a prefilled cartridge of the insulin configured to be slidably inserted into the space of the pump housing, wherein a flow path of the insulin comprises an infusion set tube that extends from the cap device to the user.

* * * * *